United States Patent
Gaska et al.

(10) Patent No.: US 12,186,440 B2
(45) Date of Patent: Jan. 7, 2025

(54) UV DEVICE FOR DISINFECTING A TARGET ENCLOSED IN A CHAMBER

(71) Applicant: Uvton, Inc., Columbia, SC (US)

(72) Inventors: Remigijus Gaska, Columbia, SC (US); Igor Agafonov, Columbia, SC (US)

(73) Assignee: UVTON, INC., Columbia, SC (US)

( * ) Notice: Subject to any disclaimer, the term of this patent is extended or adjusted under 35 U.S.C. 154(b) by 380 days.

(21) Appl. No.: 17/510,683

(22) Filed: Oct. 26, 2021

(65) Prior Publication Data
US 2022/0125969 A1 Apr. 28, 2022

Related U.S. Application Data

(60) Provisional application No. 63/105,451, filed on Oct. 26, 2020.

(51) Int. Cl.
*A61L 2/10* (2006.01)
*A61L 2/26* (2006.01)

(52) U.S. Cl.
CPC ............. *A61L 2/10* (2013.01); *A61L 2/26* (2013.01); *A61L 2202/11* (2013.01); *A61L 2202/121* (2013.01); *A61L 2202/122* (2013.01)

(58) Field of Classification Search
CPC .......... A61L 2/10; A61L 2/26; A61L 2202/11; A61L 2202/121; A61L 2202/122
See application file for complete search history.

(56) References Cited

U.S. PATENT DOCUMENTS

| | | | |
|---|---|---|---|
| 3,955,922 A | | 5/1976 | Moulthrop |
| 4,448,750 A | | 5/1984 | Fuesting |
| 5,225,172 A | | 7/1993 | Meyler et al. |
| 5,852,879 A | * | 12/1998 | Schumaier .............. F26B 9/003 34/80 |
| 7,692,159 B2 | | 4/2010 | Lane et al. |
| 2010/0326584 A1 | | 12/2010 | Wu |
| 2017/0319725 A1 | * | 11/2017 | Hann ........................ A61L 2/10 |
| 2019/0167827 A1 | * | 6/2019 | Gaska ....................... A61L 2/10 |
| 2022/0016283 A1 | | 1/2022 | Gaska et al. |

OTHER PUBLICATIONS

Casado et al., Design and validation of a LED-based high intensity photocatalytic reactor for quantifying activity measurements, Chemical Engineering Journal 327, 1043-1055 (2017) (Year: 2017).*

* cited by examiner

*Primary Examiner* — Sean M Luck
(74) *Attorney, Agent, or Firm* — JK Intellectual Property Law, PA

(57) ABSTRACT

A device for cleaning a target includes a housing including a base defining an inner circumference and a lid; a chamber within the housing having a top within the lid, a bottom within the base, and at least one UV reflective plate; at least one UV emitter attached to the housing and positioned to emit UV radiation into the chamber; and a support attached to the base and located in the chamber, the support configured for locating the target so that the UV radiation illuminates the target. The support may be formed of a plurality of ribs and/or a plurality of protrusions configured so that the target is supported thereon without falling onto the base. The at least one UV emitter may be upper and lower UV emitters, either or both of which may be one or more arrays.

22 Claims, 17 Drawing Sheets

UV DEVICE FOR DISINFECTING A TARGET ENCLOSED IN A CHAMBER

CROSS-REFERENCE TO RELATED APPLICATIONS

This application claims benefit to U.S. Provisional Patent Application No. 63/105,451, filed Oct. 26, 2020, which is incorporated by reference herein in its entirety.

TECHNICAL FIELD

The present disclosure relates generally to ultraviolet radiation, and more particularly, to a device and method for disinfection of a target, such as a sound transmission device, and the like, using ultraviolet radiation.

BACKGROUND

Reliable disinfection of sound transmission devices, such as hearing aid devices, wired and wireless transmitter/receivers including earphones, earbuds, and Bluetooth devices, etc., is a major problem. Chemical treatment using various disinfecting liquids is usually selective and eradicates some microorganisms but not all. However, chemical treatment may undesirably alter surface properties of the items under treatment. Chemical treatment without submersion and using wipes is complicated, especially for small items.

Ultraviolet (UV) radiation may be used to disinfect and operates by damaging and/or destroying DNA in a non-selective way. Different microorganisms have different doses for eradication. Eradication of microorganisms is achieved by controlling ultraviolet radiation doses to make them sufficient for eradication of most ultraviolet resistant species. Most common sources of ultraviolet light for disinfection are various lamps, primarily Mercury lamps. Disinfection devices based on Mercury lamps are bulky and can only be used as desktop devices. They generate large amounts of heat which limits disinfection exposure time and distance from irradiated object, which, in turn imposes minimum critical footprint of the devices. Mercury lamps contain hazardous materials (Mercury), use high voltage and are easy to break causing spill of Mercury and contamination of disinfection devices and irradiated objects. Sensitivity of the lamps to mechanical stress limit use of disinfection devices for travel and outdoors.

Surfaces of objects can be processed using ultraviolet light as a germicidal medium to reduce the microbial load. Water and air have been treated with ultraviolet light for quite some time to provide safe drinking water and eliminate air-borne infections and harmful pathogens. High power ultraviolet lamps have been used to disinfect surgery rooms in hospitals and sterilize medical instruments. All these applications use a variety of ultraviolet lamps, primarily low-pressure and medium-pressure Mercury lamps ranging from compact lamps for water treatment outdoors and disinfecting small devices such as HADs to massive lamp assemblies used in municipal water treatment plants. Use of such ultraviolet lamps requires complex electronics for ignition and stable operation of these high-voltage and temperature-sensitive light sources that need a significant warm up time to become fully operational. They also require special safety and handling procedures, especially during maintenance and replacement process in order to prevent glass breakup and contamination of environment with hazardous materials.

UV LED's can also be used to kill microorganisms. Peak emission wavelength of UV LED's can be adjusted during manufacturing process to provide an optimal irradiation band for eradication of specific bacteria, viruses, mold, and fungi. In general, ultraviolet light is classified into three wavelength ranges: UV-C, from about 200 nanometers (nm) to about 280 nm; UV-B, from about 280 nm to about 320 nm; and UV-A, from about 320 nm to about 400 nm. Generally, ultraviolet light, and in particular, UV-C light is "germicidal," i.e., it deactivates the DNA of bacteria, viruses and other pathogens and thus destroys their ability to multiply and cause infections and diseases. This effectively results in eradication of the microorganisms. Specifically, UV-C light causes damage to the nucleic acid of microorganisms by forming covalent bonds between certain adjacent bases in the DNA. The formation of these bonds prevents the DNA from replication, and the organism is neither able to produce molecules essential for life process, nor is it able to reproduce. In fact, when an organism is unable to produce these essential molecules or is unable to replicate, it becomes harmless.

While existing devices work for their intended purposes, it can be difficult to effectively clean all surfaces of a complex-shaped target item that may be shaped for placement on or in a user's ear without employing many LED devices, movable LED devices, complex light delivery systems, etc. Accordingly, a UV disinfection device and method that were simple, cost effective, energy efficient, or that addressed one of the drawbacks of existing disinfection systems or other issue would be welcome.

SUMMARY

According to certain aspects of the disclosure, various aspects of devices and methods and provided for disinfecting and/or and drying target items placed within a chamber of a disinfecting device. In an embodiment disclosed herein, an ultraviolet autonomous device uses UV radiation provided by UV emitters, which may be LED's, super-luminescent LED's, laser diodes, or other UV emitters.

According to certain aspects of the disclosure, a device for cleaning a target may include a housing including a base defining an inner circumference and a lid; a chamber within the housing having a top within the lid, a bottom within the base, and at least one UV reflective plate; at least one UV emitter attached to the housing and positioned to emit UV radiation into the chamber; and a support attached to the base and located in the chamber. The support may be configured for locating the target so that the UV radiation illuminates the target, the support formed of a plurality of ribs configured to fill the inner circumference so that the target is supported thereon without falling onto the base, spaces being defined between the ribs sufficient to allow air flow and light propagation through the spaces. Various options and modifications may be made.

For example, the ribs may be arranged in an intersecting grid, and/or the support may further include a plurality of protrusions extending from a top surface of the support toward the lid. A sufficient number of the ribs may be provided so that the target rests on upper tips of the protrusions rather than on the ribs. The ribs may be arranged in an intersecting grid defining a plurality of intersections, and at least some of the protrusions may be located at respective ones of the intersections.

The at least one UV reflective plate may include at least one UV reflective plate in the base of the housing and at least one UV reflective plate in the lid of the housing. The at least one UV emitter may include at least one first UV emitter located in the base of the housing and positioned to emit UV radiation into the chamber and may further include at least one second UV emitter located in the lid of the housing and positioned to emit UV radiation into the chamber. At least one of the at least one first UV emitter or the at least one second emitter may include an array of UV emitters.

According to certain other aspects of the disclosure, a device for cleaning a target may include a housing including a base defining an inner circumference and a lid; a chamber within the housing having a top within the lid, a bottom within the base, and at least one UV reflective plate; at least one UV emitter attached to the housing and positioned to emit UV radiation into the chamber; a support attached to the base and located in the chamber, the support configured for locating the target so that the UV radiation illuminates the target, the support includes a plurality of protrusions extending from a top surface of the support toward the lid for supporting the target therein thereon without falling onto the base. Various options and modifications are possible with this device as well.

For example, the support may be formed of a plurality of ribs configured to fill the inner circumference so that the target is supported thereon without falling onto the base, spaces being defined between the ribs sufficient to allow air flow and light propagation through the spaces, the ribs being arranged in an intersecting grid defining a plurality of intersections, and at least some of the protrusions are located at respective ones of the intersections. Also, the at least one UV reflective plate may include at least one UV reflective plate in the base of the housing and at least one UV reflective plate in the lid of the housing, and the at least one UV emitter may include at least one first UV emitter array located in the base of the housing and positioned to emit UV radiation into the chamber and may further include at least one second UV emitter array located in the lid of the housing and positioned to emit UV radiation into the chamber.

According to other aspects of the disclosure, a device for cleaning a target may include a housing including a base and a lid; a chamber within the housing having a top within the lid, a bottom within the base; at least one UV reflective plate in the base of the housing; at least one UV reflective plate in the lid of the housing; at least one first UV emitter located in the base of the housing and positioned to emit UV radiation into the chamber; at least one second UV emitter located in the lid of the housing and positioned to emit UV radiation into the chamber; and a support attached to the housing and located in the chamber, the support configured for locating the target so that the UV radiation from the at least one first UV emitter and the at least one second UV emitter illuminates the target. Again, various options and modifications are possible.

For example, the at least one first UV emitter may include an array of UV emitters and/or the at least one second UV emitter may include at least one array of UV emitters.

The at least one UV reflective plate in the lid may include a main plate and a side plate extending circumferentially around the main plate, the at least one second UV emitter including a first array of UV emitters in the main plate and a second array of UV emitters in the side plate. If so, the first array of UV emitters and the second array of UV emitters may be circumferentially interleaved with each other.

The support may be at least one of translucent, transparent, reflective, or formed with openings for transmitting UV light therethrough.

The at least one first UV emitter and the at least one second UV emitter may each include a UV LED or a waveguide outlet for a UV LED.

BRIEF DESCRIPTION OF THE DRAWINGS

These and other features of the disclosure will be more readily understood from the following detailed description of the various aspects of the disclosure taken in conjunction with the accompanying drawings that depict various aspects of the disclosure.

DETAILED DESCRIPTION

Figure 1:
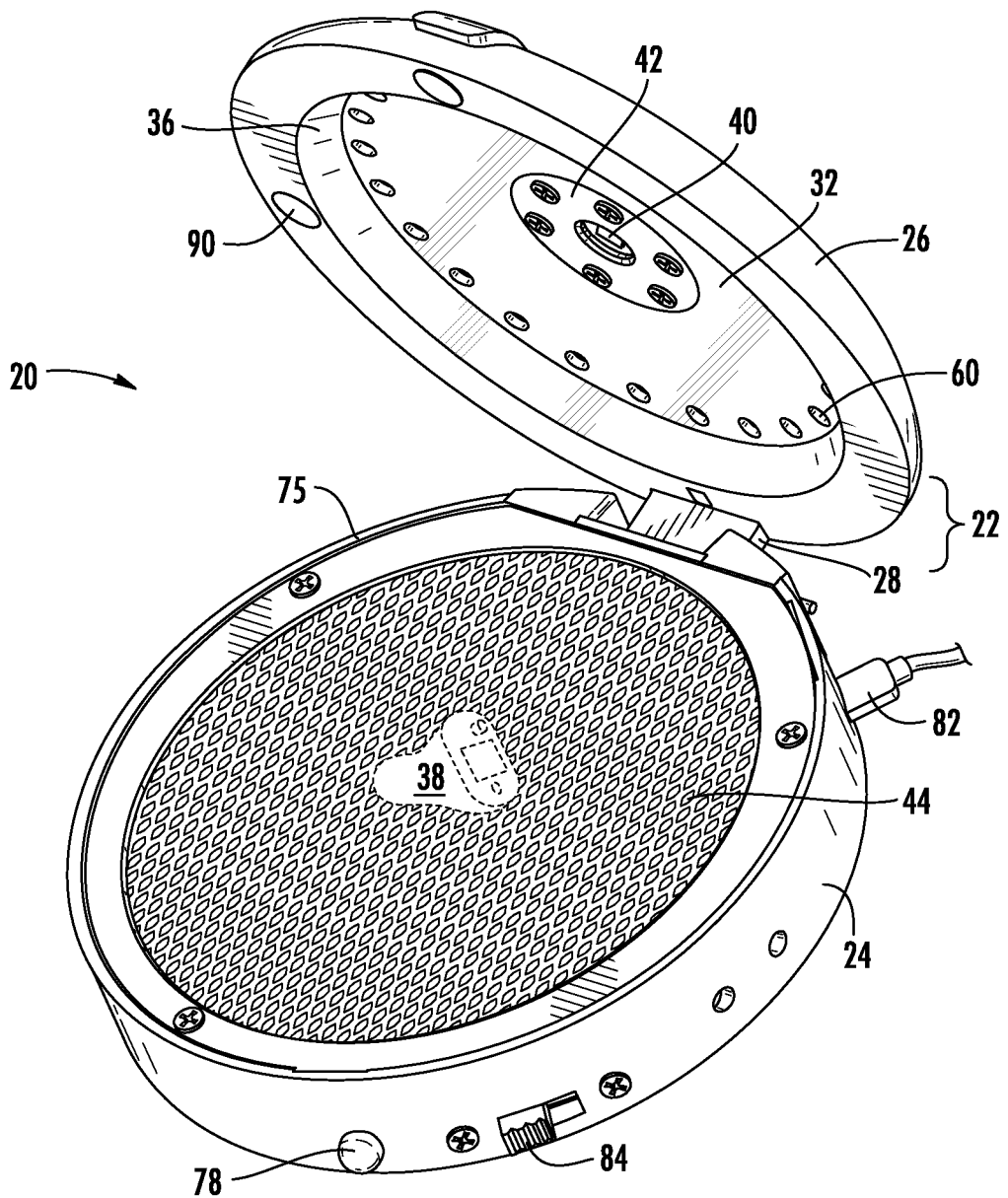
FIG. 1 is an isometric view of one example of a portable and autonomous ultraviolet disinfection and/or drying device with its lid opened, showing a UV LED mounted in the center of the device lid and a perforated support for the target item(s) to be disinfected and/or dried.
Figure 2:
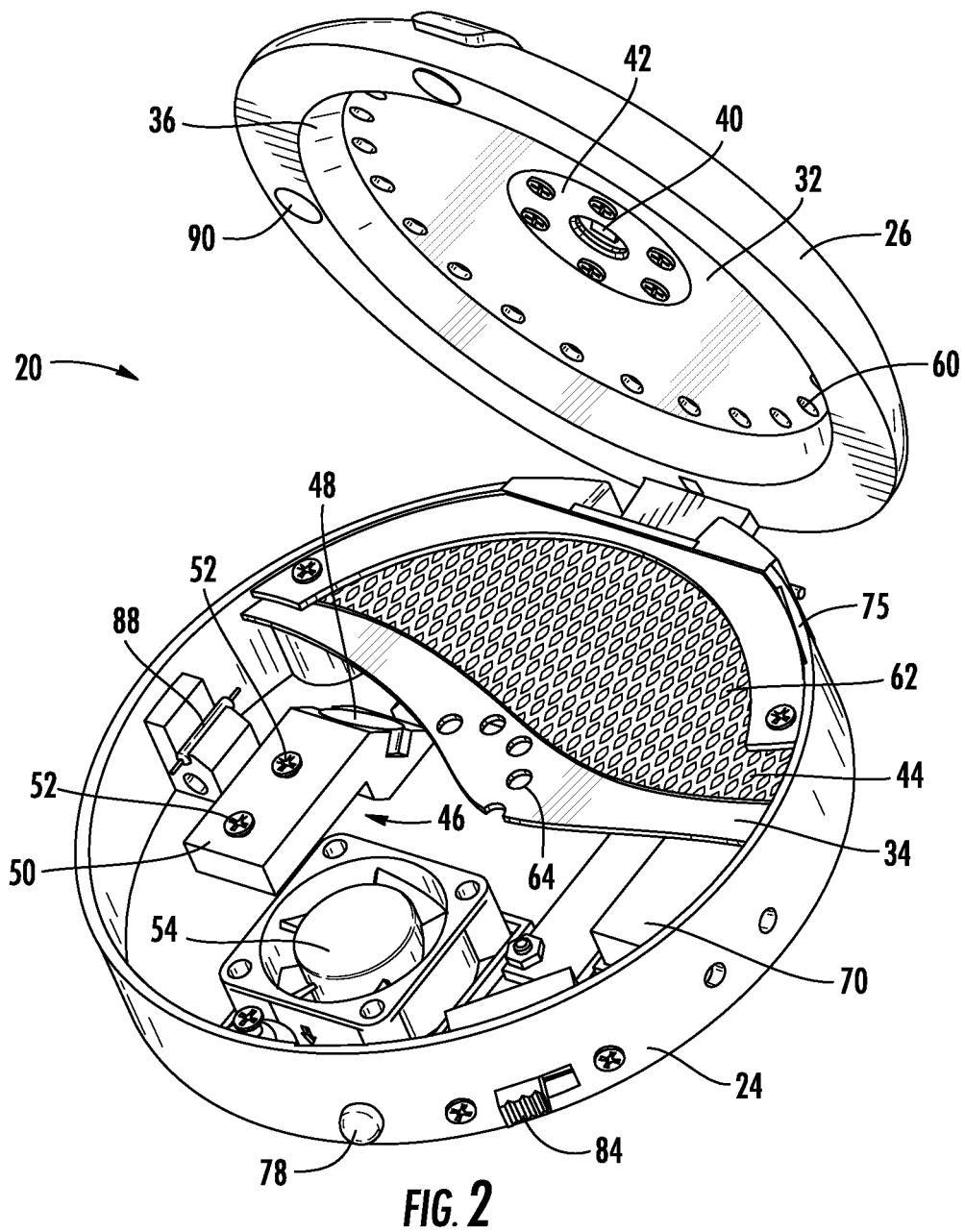
FIG. 2 is a partially broken-away isometric view of the device of FIG. 1, showing a vibration actuator, bottom UV reflective surface, air fan and other internal components.

Detailed reference will now be made to the drawings in which examples embodying the present disclosure are shown. The detailed description uses numeral and letter designations to refer to features in the drawings. Like or similar designations in the drawings and description have been used to refer to like or similar parts of the disclosure.

The drawings and detailed description provide a full and enabling description of the disclosure and the manner and process of making and using it. Each embodiment is provided by way of explanation of the subject matter not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

Generally speaking, the present disclosure is directed to various embodiments of a disinfection, cleaning, and/or drying device and method using UV radiation. As shown in FIGS. 1-10, a first embodiment 20 of such a device includes a housing 22 which may have a base 24, a lid 26 attached to the base by a hinge 28. Within device 20 is a chamber 30 (see FIG. 7), a first UV reflective plate 32 in lid 26, and a second UV reflective plate 34 in base 24. A third (or fourth, etc.) UV reflective surface 36 may be formed in lid 26 (as shown) or base 24 to provide a substantially continuous reflective chamber 30 for generally enveloping a target item 38 such as a sound transmission device, hearing aid device, wired and wireless transmitter/receiver, earphone, earbud, Bluetooth device, or other similar sized and/or purposed device, etc. Plates 32,34 may be curved, for example parabolic or substantially parabolic, and may have identical or differing curvature. However, one or both plates 32,34 may be flat.

At least one UV emitter, in this case an LED 40, is attached to housing 22, in this case first UV reflective plate 32, and is positioned to emit UV radiation into chamber 30. UV LED 40 may be formed in an assembly including typical electric connections and controls (not shown) and a heat sink 42 for removing heat generated by the UV LED.

A support 44 is attached to housing 22 and is located in chamber 30 between first UV reflective plate 32 and second UV reflective plate 34. Support 44 locates target 38 between first UV reflective plate 32 and second UV reflective plate 34 so that the UV radiation illuminates the target. Support 44 as shown is a perforated, mesh-like structure extending substantially across chamber 30 within base 24 when lid 26 is closed.

Figure 8:
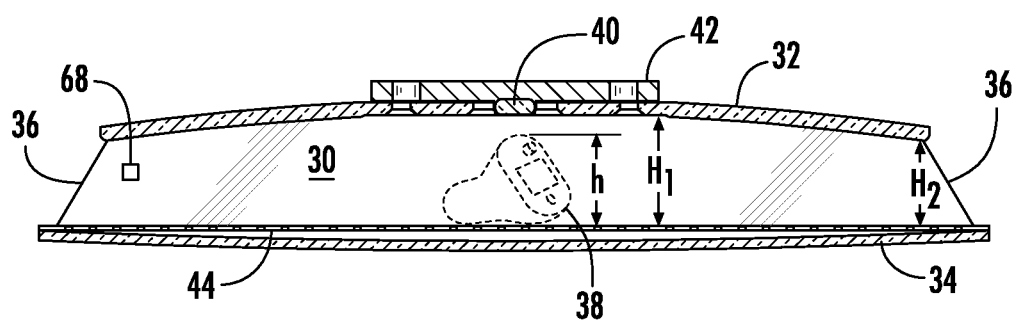
FIG. 8 is a close-up cross-sectional view of the chamber portion of FIG. 7.

As shown in FIG. 8, near the center of support 44 and UV LED 40, a spacing of a predetermined distance H1 exists between the support and top of chamber 30 (as defined here by first UV reflective plate 32). Toward the periphery of support 44, a predetermined distance H2 exists between these elements. As Illustrated, H2 is smaller than H1, as the curvature of plate 32 helps with reflection of UV radiation within chamber and toward target 32. However, plate 32 need not be used and/or need not be curved, so H2 need not be smaller than H1. As also illustrated, at least H1, and optionally both H1 and H2 may be larger than h, a height of target 32 (optionally a maximum height depending on orientation of target on support 44). Such dimensioning also assists in directing UV illumination toward and onto target 32. As discussed in more detail below, such dimensioning allows for vibrational movement of target 32 relative to support 44 UV LED 40 and chamber in general 30.

Figure 3:
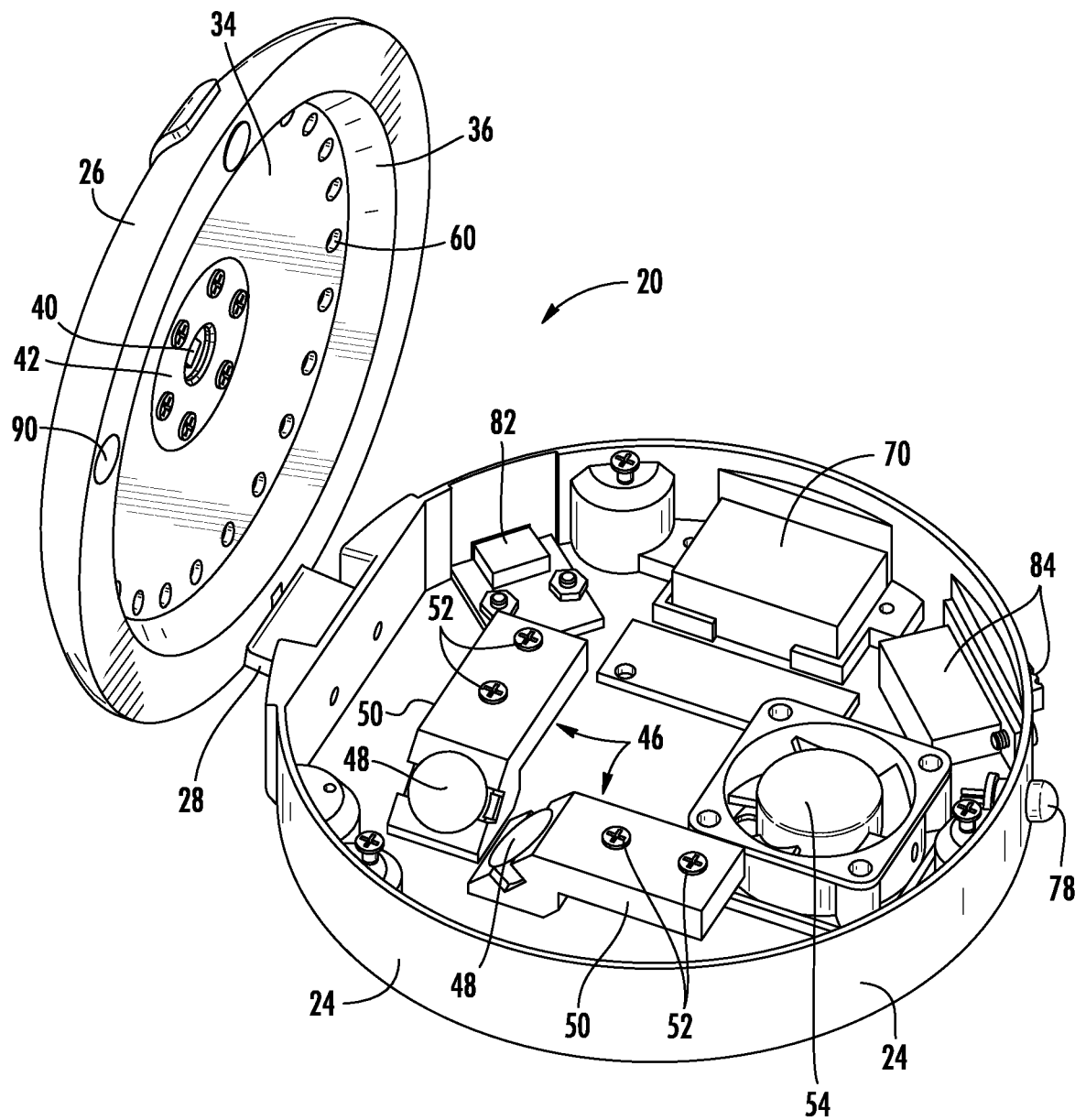
FIG. 3 is an isometric view of the device of FIG. 1, with the support and bottom UV reflective surface removed to show further internal components.
Figure 4:
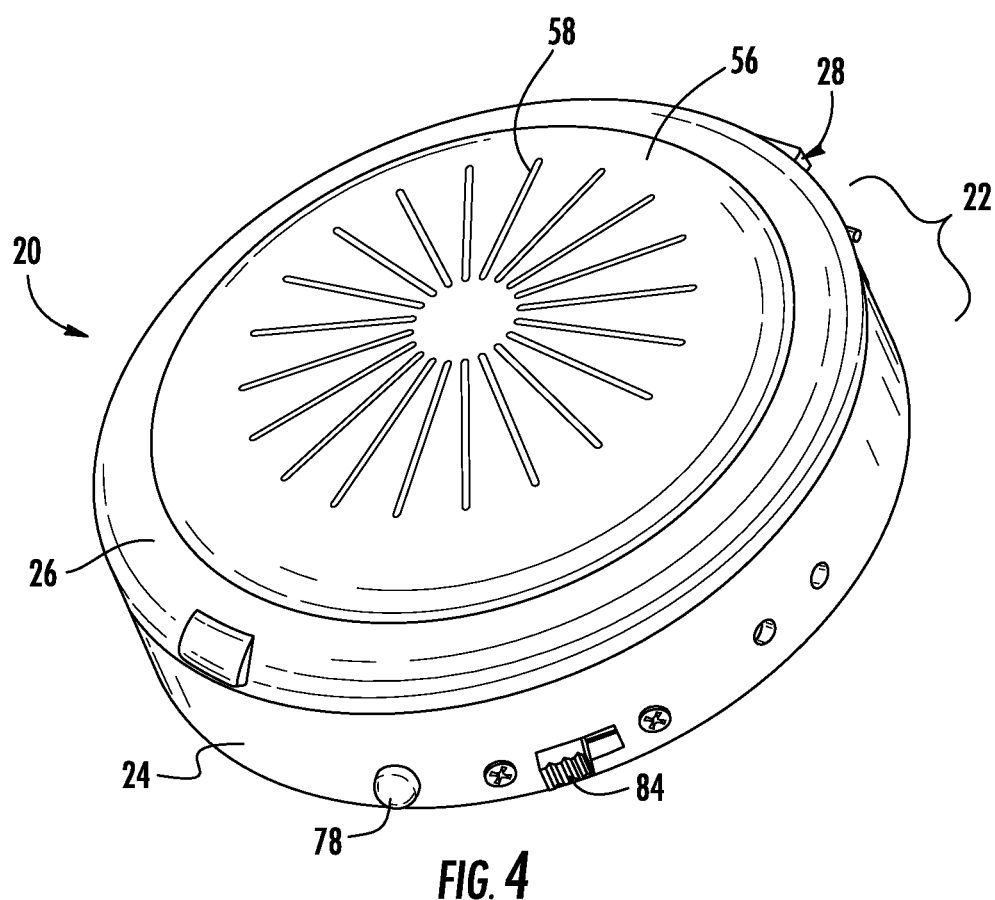
FIG. 4 is an isometric view of the device of FIG. 1, with the lid closed, showing air gaps in the cover of the lid.
Figure 5:
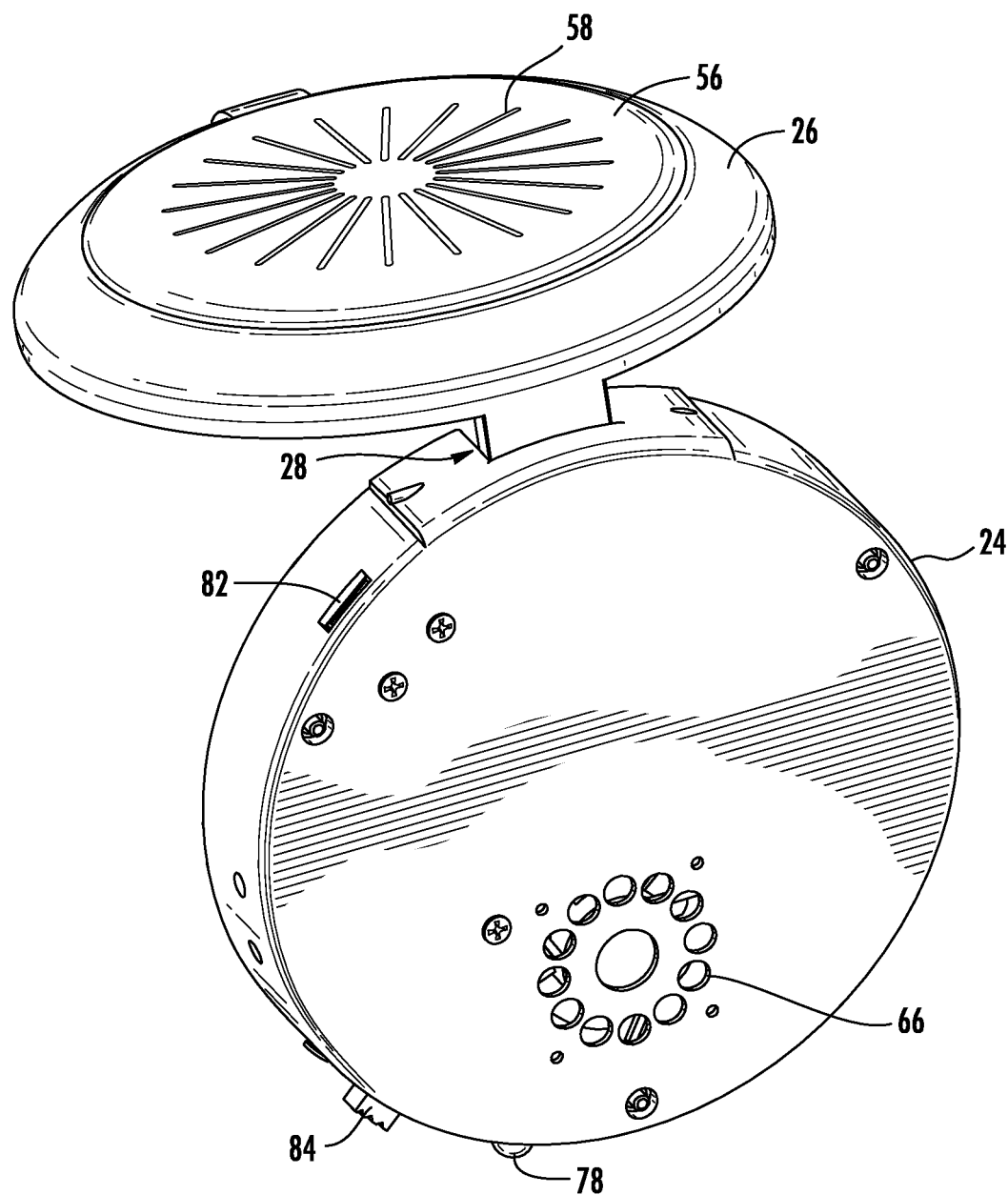
FIG. 5 is a bottom isometric view of the device of FIG. 1, showing air gaps in the bottom of the base of the device.
Figure 6:
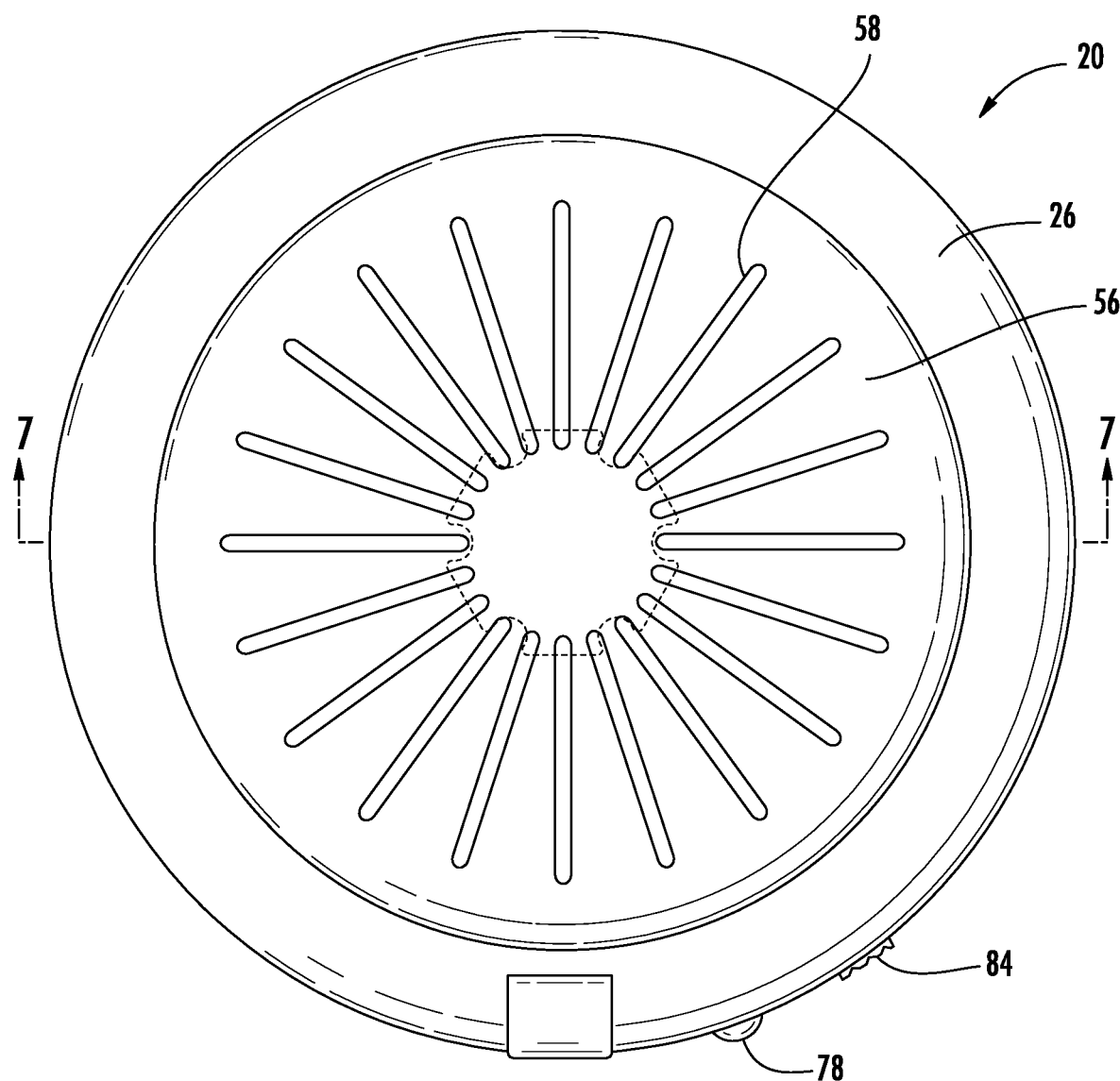
FIG. 6 is a top view of the device of FIG. 1.
Figure 7:
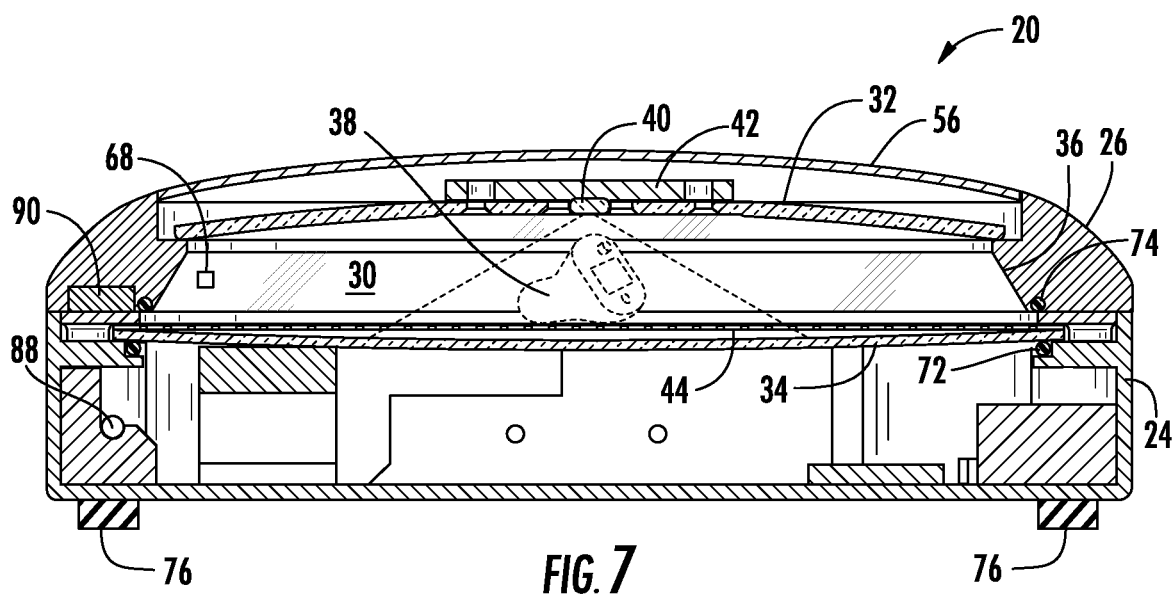
FIG. 7 is a cross-sectional view of the device of FIG. 1 taken across line 7-7 in FIG. 6, showing a chamber within the device defined by UV reflective surfaces, a UV LED and a target item on a support, and showing O-rings for radiation, moisture, and flow confinement and/or vibration control, as well as vibration control pads.
Figure 10:
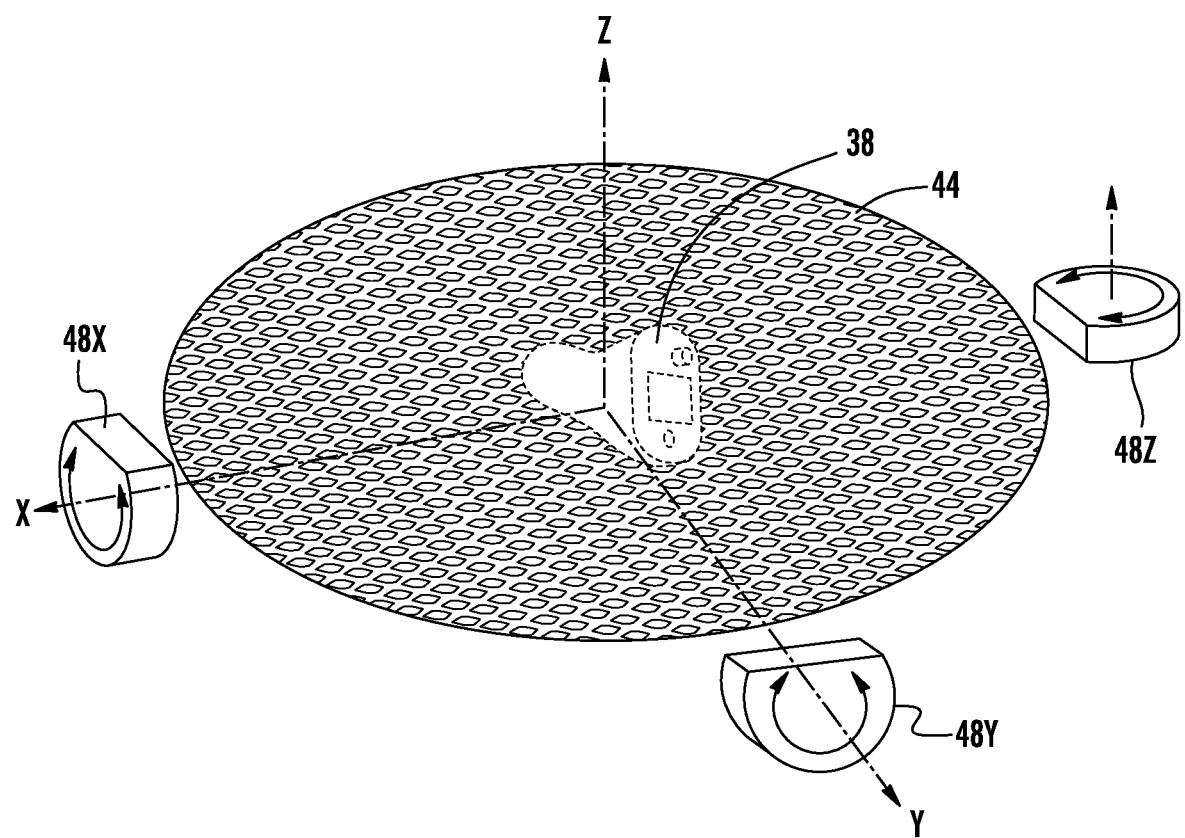
FIG. 10 is a schematic view showing that actuators may operate linearly or rotationally along three perpendicular axes relative to a target item on the support of FIG. 1.

At least one actuator 46 may be attached to housing 22, in this case base 24, and is positioned to move target 38 relative to support 44 while UV LED 40 emits UV radiation. As shown in FIG. 3, two such actuators 46 may be provided, mounted in opposing directions so as to create movement in differing planes. As illustrated, each actuator 46 may be a vibro-actuating motor 48 attached by a mount 50 to base 24, and attached to second UV reflective plate 34 by screws 52. Each vibro-actuating motor 46 may create linear motion and/or rotational motion. FIG. 10 shows three such motors 48$x$, 48$y$, and 48$z$, providing linear and/or rotational movement relative to the common x, y, and z axes. Alternatively, actuators 46 may also comprise piezoelectric actuators. Actuators 46 are provided to create motion and/or vibration sufficient to move target 38 relative to UV LED so as to provide differing illumination of the target over time, so as to reduce or eliminate non-uniform irradiation of the target 38. If desired, such movement can be of a frequency and amplitude to turn over, rotate, etc., the target 38 so as to provide coverage of more if not all surfaces of the target. Use of a highly reflective chamber 30 as described above assists with improving UV LED radiation of such coverage so that more uniform coverage is achieved.

Configuring chamber 30 so that at least the center portion near UV LED 40 has a predetermined spacing of H1 greater than a height h of target 32 enables the one or more actuators 46 provided to move target 32 relative to support 44. Further, if at least H1, if not H2 or other portions are greater than at least 1.25 or at least 1.5 times h, the ability to achieve such movement may be enhanced. Moreover, having at least H1 be greater than h by such amounts can assist substantially in allowing target 32 to flip over due to the vibrations of the at least one actuator 46. If target 32 is a hearing aid, such devices come in many styles (e.g., in the canal, completely in the canal, in the ear, behind the ear, receiver in canal, receiver in ear, open fit, etc.). Such devices vary in size, both within styles and between styles, as do other target such as earbuds, Bluetooth devices, etc. Thus, H1 may be as small as 0.5 inches for relatively smaller targets, but H1 more likely to allow for vigorous movement and/or flipping of target 38 or use with a larger target or a range of differently-sized targets at higher sizes, such as 1.0 inches, 1.25 inches, 1.5 inches, 2.0 inches, 3.0 inches, or more, etc. A balancing of H1 to H2 ratios, taking into account the curvature of UV plate 32 or chamber top, depending on desired reflection pattern and overall size of device 20, can also factor into the dimensioning of H1, H2, curvature of UV plate 32, etc. For example, H1 can be greater than H2, 1.25 times greater, 1.5 times greater, or more, etc.

If desired, one or more actuators 46 can be mounted at or in contact with any location within device 20, such as base 24, lid 26, surfaces 32,34,36, UV LED/heat sink assembly 40/42, support 44, etc. Such actuators can be used to move/deform/vibrate the reflective surfaces, the UV LED, the support, etc.

The UV LED 40 selected as the UV emitter can be a single UV LED or multiple UV LED's, or one or more UV LED's with multiple chips, with a common or independent control of each UV LED and/or chip. UV LED peak emission wavelength is in UV-C spectral range with a wavelength range of between 200 nm to about 285 nm, however, ranges may also be about 200 nm to about 235 nm and about 255 nm to about 285 nm which are effective against certain microorganisms. While susceptibility to UV light varies, exposure to UV energy for about 20 to about 34 milliwatt-seconds/cm2 is adequate to deactivate approximately 99 percent of most pathogens. Other parameters may be used, however. As discussed below, a controller can be used to alter the timing and power of the UV LED.

If disinfection (i.e., deactivating 99%, 99.9%, 99.99%, etc., but not 100% as in sterilization) is the goal, use of UV LED's may be particularly attractive because of their lower power need and heat generation, and desirable spectral wavelengths. Devices can be made smaller, as long as sufficient coverage of the target is achieved. Therefore, one or more strategies like use of multiple UV LED's, arrays of UV LED's, UV LED's above and below the target, reflective surfaces surrounding the chamber, supports that allow light transmission and/or reflection, supports that influence the target to stay in a desired location, vibrations or fans to move the target around or flip the target on the support, or others may be employed to increase light coverage on the target and to prevent lack of disinfection on areas that may be within shadows (for example, as compared to a device with a single UV LED above a stationary target). Use of a "cold" UV LED with frequencies between 255 nm and 285 nm provides particular utility in terms of low power, high frequency, and low heat generation for disinfection. As compared to a conventional UV quartz sterilization device at 253.7 nm with its relatively larger amount of power usage and heat generation, the devices disclosed herein provide effective near-sterilization disinfection, in a small, cost effective, and low energy usage form factor relative to the target.

Alternatively, the UV emitter(s) may further include or instead include a super-luminescent (SLED or SLD), a laser diode (LD), or any other UV source providing emissions suitable for control of microorganisms, as mentioned above, whether entirely within the above spectral ranges or within other ranges.

A super-luminescent diode is an edge-emitting or vertically-emitting semiconductor light source. It combines the high power and brightness of laser diodes with the low coherence of conventional light-emitting diodes. A super-luminescent light emitting diode is, similar to a laser diode, based on an electrically driven pn-junction that, when biased in forward direction, becomes optically active and generates amplified spontaneous emission (stimulated emission) over a wide range of wavelengths. The peak wavelength and the intensity of the SLED depend on the active material composition and on the injection current level. SLED's are designed to have high single pass amplification for the spontaneous emission generated along the waveguide but, unlike laser diodes, insufficient feedback to achieve lasing action. This is obtained very successfully through the joint action of a tilted waveguide and anti-reflection coated facets.

A laser diode is a semiconductor device that emits light through a process of optical amplification based on the stimulated emission of electromagnetic radiation. The main difference compared to SLEDs is a strong feedback that occurs in the optical cavity in between anti-reflection coated facets designed for multi-pass amplification. Optical amplification occurs in the cavity under injected electric current sufficient to create so called "inversion-population."

Support 44 may be a continuous perforated holder, as illustrated to allow light transmission therethrough. Alternatively, it may be a transmissive, transparent, and/or or UV reflective material. Thus, support 44 may be a discontinuous UV reflective member including material selected from Aluminum, UV-enhanced Aluminum, Aluminum Oxide Aluminum, and UV-enhanced Aluminum Oxide Aluminum, or it may include a UV-transparent polymer selected from FEP, EFEP, PLA, and LDPE. Support 44 may include a discontinuous member, a perforated member, a grid, a mesh, a weave, etc. Support 44 may include a plurality of openings for transmitting emitted UV radiation therethrough, as well as allowing airflow therethrough. Support 44 may be removable (e.g., by removing screws, by a snap fit, etc.) for cleaning the support, plate 34, and/or base 24.

A fan 54 may be located within housing 22, for example within base 24, for pulling air through housing 22 past target 38 to assist in drying the target. One flow path is as follows: lid cover 56 may have openings 58, first plate 32 may have openings 60, support 44 may have openings 62, plate 34 may have openings 64, and base 24 may have openings 66. However, other openings and flow paths are possible thorough housing 22 upstream and downstream of fan 54. The air-flow may go in either direction (lid-to-base or base-to-lid), or may be through lid only or base only, and need not go past or through support 44. Thus, if desired, fan 54 may pull air past UV LED 40 and remove heat generated by the UV LED (from heat sink 42 if present) to assist in drying target 38. Fan 54 may be operated continuously, intermittently, before or after the UV LED, based on a sensed temperature, moisture, or humidity level, etc., and may be stopped, started, adjusted, or modulated as desired.

Device 20 may include at least one UV radiation monitoring structure 68, which may be a sensor (as shown) or may be a window (not shown) though base 24 and/or lid 26. Sensor 68 located within housing 22 may be for example a photodetector for sensing UV radiation and communicating a corresponding signal to a controller 70 located within the housing. Sensor 68 may be a single UV photodetector and/or multiple UV photodetectors with different spectral responses. UV LED emission of parasitic visible light, predominantly close to blue, yellow, or white for example may be monitored. If UV monitoring structure 68 is a window, it may be a UV blocking window located in the housing with a material that transmits a parasitic visible light emitted by the UV LED, or it may include a fluorescing material activated by the UV LED to transmit a fluorescent visible light. The window may block UV radiation and transmit white light or visible light with wavelength longer than 400 nm. Lack of sensed emission, visible light, fluorescence, etc., indicates failure of the UV LED radiation source and/or the device in general. Also, indicator LED's 78, 80 may be provided on outside of housing 22 to indicate for example, power on, UV LED on, fan on, cleaning in progress, cleaning complete, etc.

Device 20 may include elements for vibration isolation and UV blocking. O-rings 72, 74 may be located in base 24 and lid 26 to reduce vibration of the device. Vibration isolation pads 76 are attached to the bottom of base 24. O-rings 72, 74 may also assist in blocking UV radiation from escaping radially out of device 20, and a small annular wall 75 on one or both of base 24 and lid 26 may also assist in such blocking.

Figure 9:
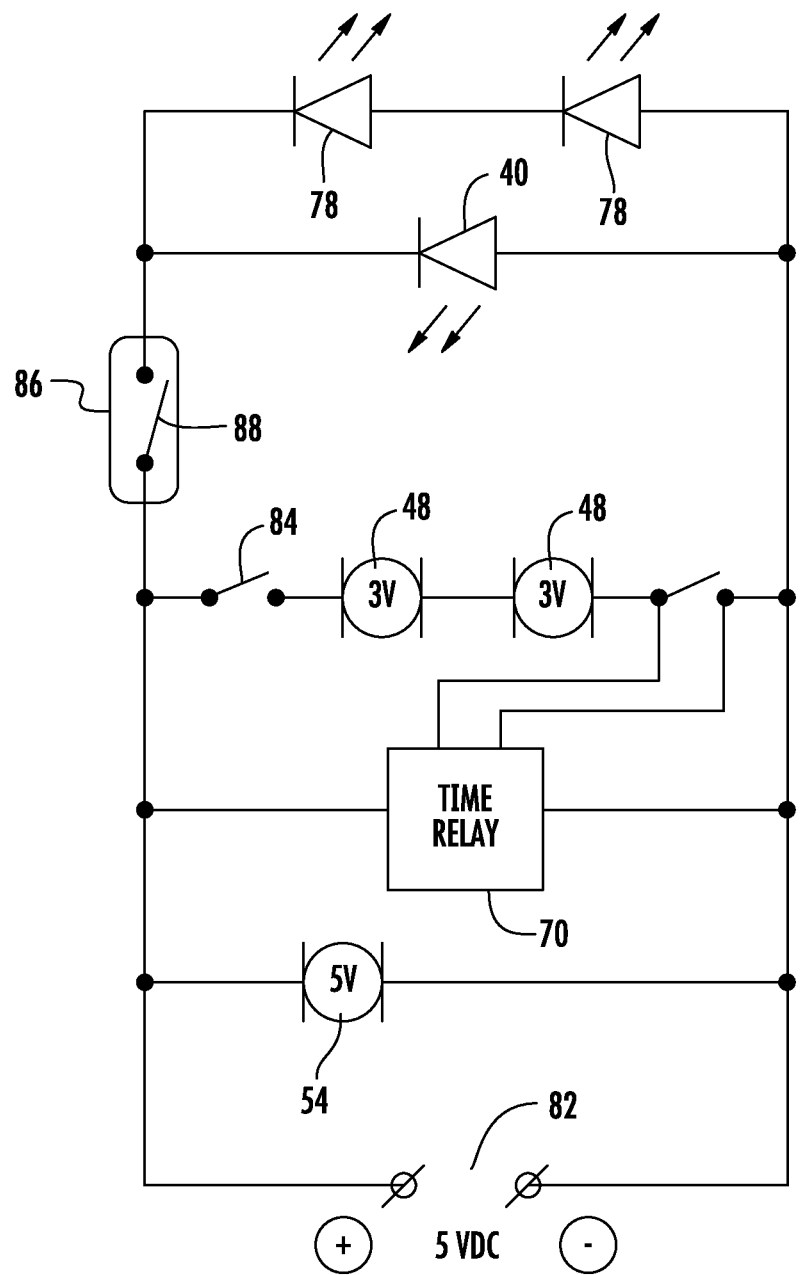
FIG. 9 is an example of one possible circuit diagram for the device of FIG. 1.

The electrical connections of elements of device 20 are omitted for clarity, but are shown schematically in FIG. 9.

As illustrated, controller 70 may be provided as hard-wired circuitry on a printed circuit board within the housing for controlling the at least one UV LED 40, actuator 46, and the device in general. Device 20 may be powered via a USB-type connector providing 5 VDC power. The device could also be powered by an external battery or an internal rechargeable battery. Fan 54 may also be 5 VDC, and may draw about 0.2 A at 10,000 rpm, moving 2.6 cfm. Vibro-actuator motors 48 may operate at 3 VDC and 0.05 A, to provide vibrations at 120-150 HZ with an amplitude of 0.5 g. On-off switch 84 may be provided on housing 22 for the user to operate. Controller 70 may include a timer relay with programming in memory, or solid state or other logic control to control the operation of the disclosed elements. A cover-open sensor 86 may be provided to turn off device 20 in total, or just UV LED 40, or to simply provide a signal to controller 70 if lid 26 is raised. Sensor 86 may include a reed switch 88 and a magnet 90 or another sensor, such as electronic, electromagnetic, optical, physical, etc. Sensors may be provided throughout device 20 as noted above (but not shown in FIG. 9) and connected to the controller 70 as needed.

Controller 70 may send signals to UV LED 40 to control at least one of the intensity, wavelength, duration, and schedule of the emitted UV radiation. A temperature sensor may be provided in communication with controller 70, with the controller sending control signals to UV LED 40 based on a signal received from the temperature sensor so as to achieve a desired temperature. Controller 70 may control a speed of fan 54 so as to achieve a desired air flow through the housing. Controller 70 can be used to operate device 20 sufficiently to sanitize target 38. For hearing aid devices, 15-20 minutes may be sufficient, although longer times may be used. For certain organisms, cycling may improve disinfection rates to avoid photo-reactivation. Device 20 can be run overnight at a set time (if controller 70 and/or device 20 includes a clock/timer function). Accordingly, many different modes of operation may be selectable, either by hard-wiring or programming them into controller 70, or by providing switching or other user input-output devices for user indication of desired operation.

According to certain other aspects of the disclosure, a method for cleaning a target 38 may include the steps of supporting the target 38 on a support 44 in a chamber 30 in a housing 22, the chamber defined by first and second UV reflective plates 32,34; operating at least one UV LED 40 attached to housing 22 and positioned to emit UV radiation into chamber 30 so that the UV radiation illuminates target 38; and operating an actuator 46 to modify the UV radiation illumination of target 38 while UV LED 40 is operated. Actuator 46 may move target 38 relative to support 44 while operating, and/or may deform and thereby change a curvature of at least one of first and second UV reflective plates 32,34 while operating, and/or may move UV LED 40 relative to housing 22 when activated.

It should be understood that device 20 and accordingly the above-described method may be modified in various ways, such as, for example, by changing the shape of or eliminating any one, two, or all of UV reflective plates 32,34,36, by modifying the surface profile of support 44 (for example, by including a depression to help keep the target centered beneath the UV LED), by providing vertical vibration (in combination or alone) sufficient to cause the target to flip over on the support, by configuring actuator mount 50 in different ways or by connecting the actuator mount to different elements (including support 44), by providing an air flow from fan 54 (or an additional fan) to help keep the target centered beneath the UV LED, by using or adding an alternate UV emitter, etc.

Figure 11:
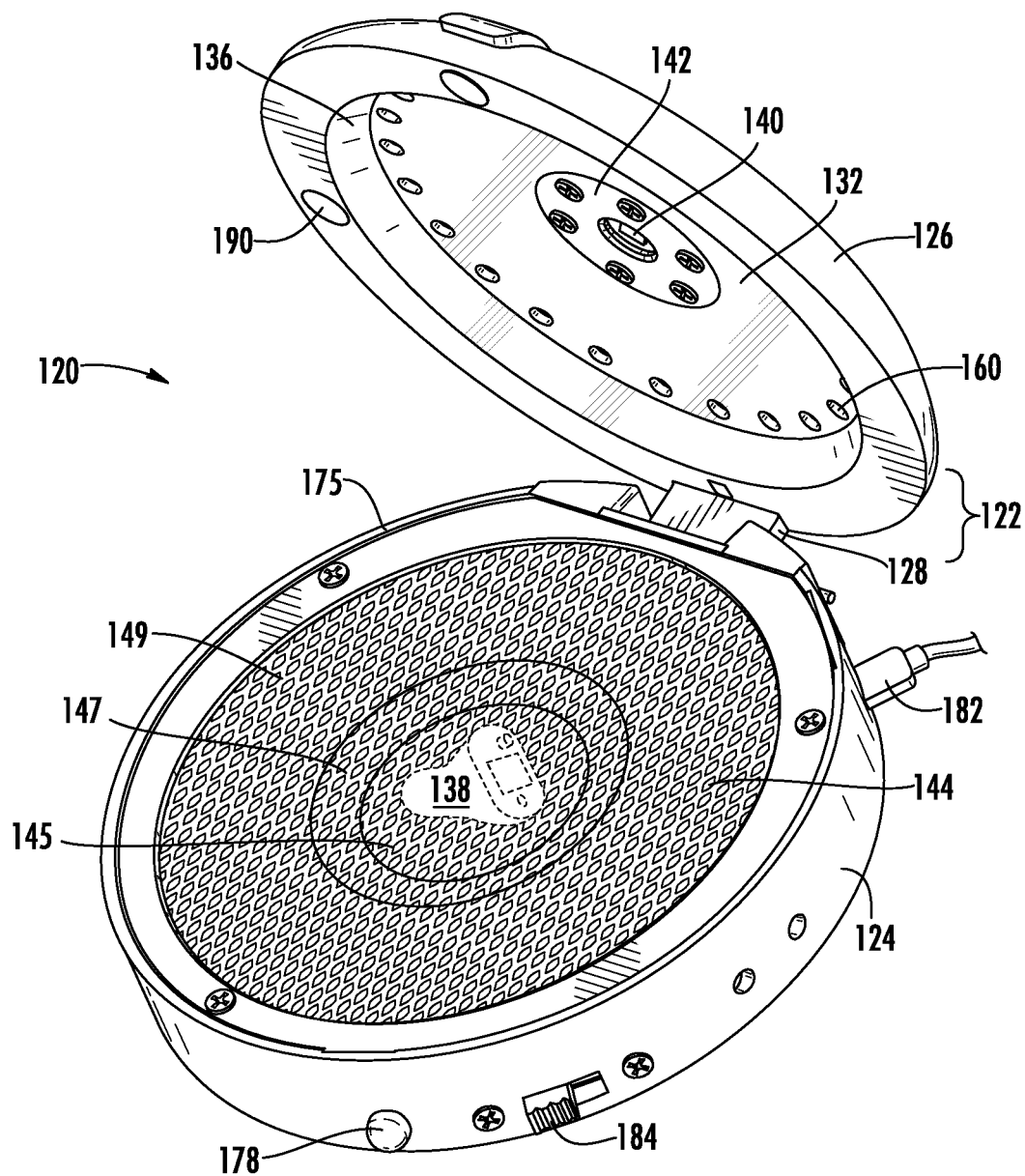
FIG. 11 is a schematic view showing a modified version of the device of FIG. 1.
Figure 12:
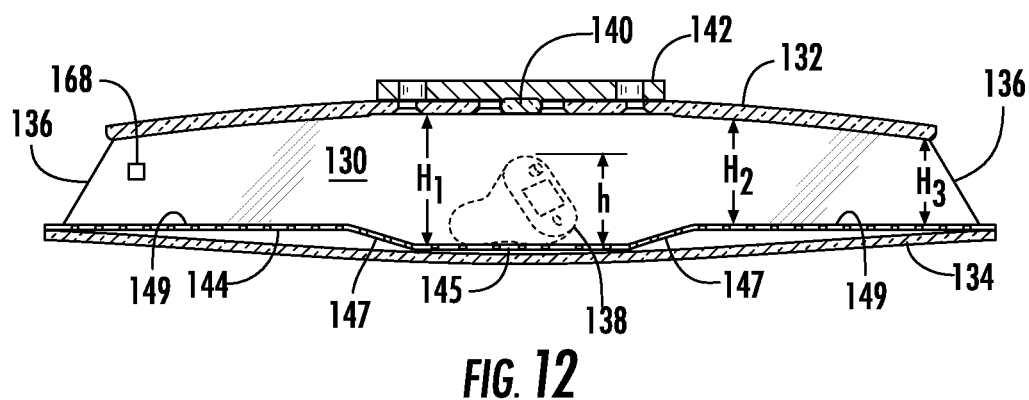
FIG. 12 is a close-up cross-sectional view of a portion of the chamber portion of the device of FIG. 11.

FIGS. 11 and 12 show an additional embodiment of a device 120 for cleaning a target 138. For brevity and clarity, like and similar reference numerals in the 100 series are used in the figures to refer to like and similar elements of device 120, although not all mentioned herein. Differences between embodiments will be highlighted.

As illustrated, device 120 includes a housing 122, a chamber 130 within the housing having a top defined by UV reflective plate 132, and a bottom defined by UV reflective plate 134. The UV emitter, in this case an LED 140 but also possibly adding or substituting another type of UV emitter as noted above, is located to emit UV radiation into chamber 130, and a support 144 is attached to housing 122. Support 144 is located in the chamber 130 so as to be spaced from the top by a predetermined distance (varying between H1, H2, and H3) sufficient to allow target 138 (with height h) to flip within the chamber.

Support 144 is configured for locating target 138 so that the UV radiation illuminates the target. Support 144 may be flat as in device 20 above, or it may be non-flat as in device 120. As illustrated in FIGS. 11 and 12, support 144 includes a top surface defining a depression 145 configured for receiving target 138 and gravitationally urging the target toward a location in which the UV radiation illuminates the target (e.g., toward UV LED 140). As shown, depression 145 is located generally vertically beneath UV LED 140 in chamber 130. Slanted sides 147 around depression angle upwards to periphery 149. Use of slanted sides 147 assist with gravitational urging of target 138 toward depression 145 from periphery and/or help maintain the target within the depression as vibration occurs. Such configuration to assist with maintaining target 138 in position to receive UV radiation can be helpful in efficiently irradiating the target. Such configuration can be particularly useful, but is not required in all embodiments, in devices in which actuators operate vigorously enough to flip over target 138 within chamber 130.

It should be understood that support 144 can be configured in other non-flat shapes than elements 145/147/149 as illustrated to assist with locating target 138. For example, and of portions 145/147/149 need not be linear or flat in cross-section as illustrated. Support 144 could be continuously curved from periphery of support 144 toward center of the support with a curve approximating or with greater radius of curvature than plate 134. Portions 145/147/149 can be of different radius on support 144 relative to each other or support 144 in general. Portions 145 and 147 could be combined into a continuous curve or conical slant rather than the illustrated conical slant (147) and flat (145). If desired, housing 122 may be configured so that the predetermined distance (H1, H2 and/or H3) is adjustable, wherein the location of some or all of support 144 is adjustable relative to the top of chamber 130. Such could be achieved by providing a support 144 movable relative to base 124, or a single part or multi-part support that is itself reconfigurable, bendable, slidable, articulable, etc.

These and other modified configurations cold be used with support 144 to assist in locating target in a desired orientation nearer UV LED, although a flat support as in support 44 could be used as well. Also, in some respects as in the claims below, a reflective plate such as plate 134 could be considered the support, and a separate support such as element 144 could be eliminated. Use of structures to assist in locating target 138 nearer UV LED 140 can provide better instantaneous radiation coverage of the target. Accordingly, a shorter total duration of illumination may be required, a weather LED may be employed, etc., to save time, electricity, etc., in some respects.

If desired, a protecting coating may be provided on or between one or more of UV reflective plates 132, 134, 136, in particular, any plate that might be contacted by target 138 during vibrational moving. Thus, a protecting covering such as a continuous or discontinuous UV transparent polymer, coating, etc. can be applied to any surface desired, including those that might be contacted by target 138. Such includes an embodiment where plate 134 itself acts as support, as noted above.

If desired, openings in plate 134 (either in addition to openings such as 64 in FIG. 2, or by moving openings 64) may be provided radially outwardly of support portions 145 and/or 147 (if present) to assist in moving air output by a fan (such as fan 74) inwardly, thereby assisting in maintaining target 138 centrally in a desired position relative to UV LED 140. A second fan may be provided for such air flow, with a second and/or different flow path as compared to fan 74. Also, the target-aligning flow may pass through other portions of base 124 and/or lid 126, and not necessarily through plate 134.

One or more actuators as discussed above may be employed with device 120. Actuators may be attached for direct movement of plates 132, 134, support 144, base 24, lid 26, etc. Actuator(s) may operate as above, and may operate with sufficient frequency and amplitude so as to move and/or flip over target 138 on support 144 during operation.

A controller as discussed above may be employed for controlling UV 140 LED and the actuator(s), wherein the controller sends signals to the UV LED to control at least one of the intensity, wavelength, duration, and schedule of the emitted UV radiation, wherein the controller sends signals to the actuator to control at least one of the frequency, amplitude, duration, and schedule of the vibration of the actuator.

Figure 13:
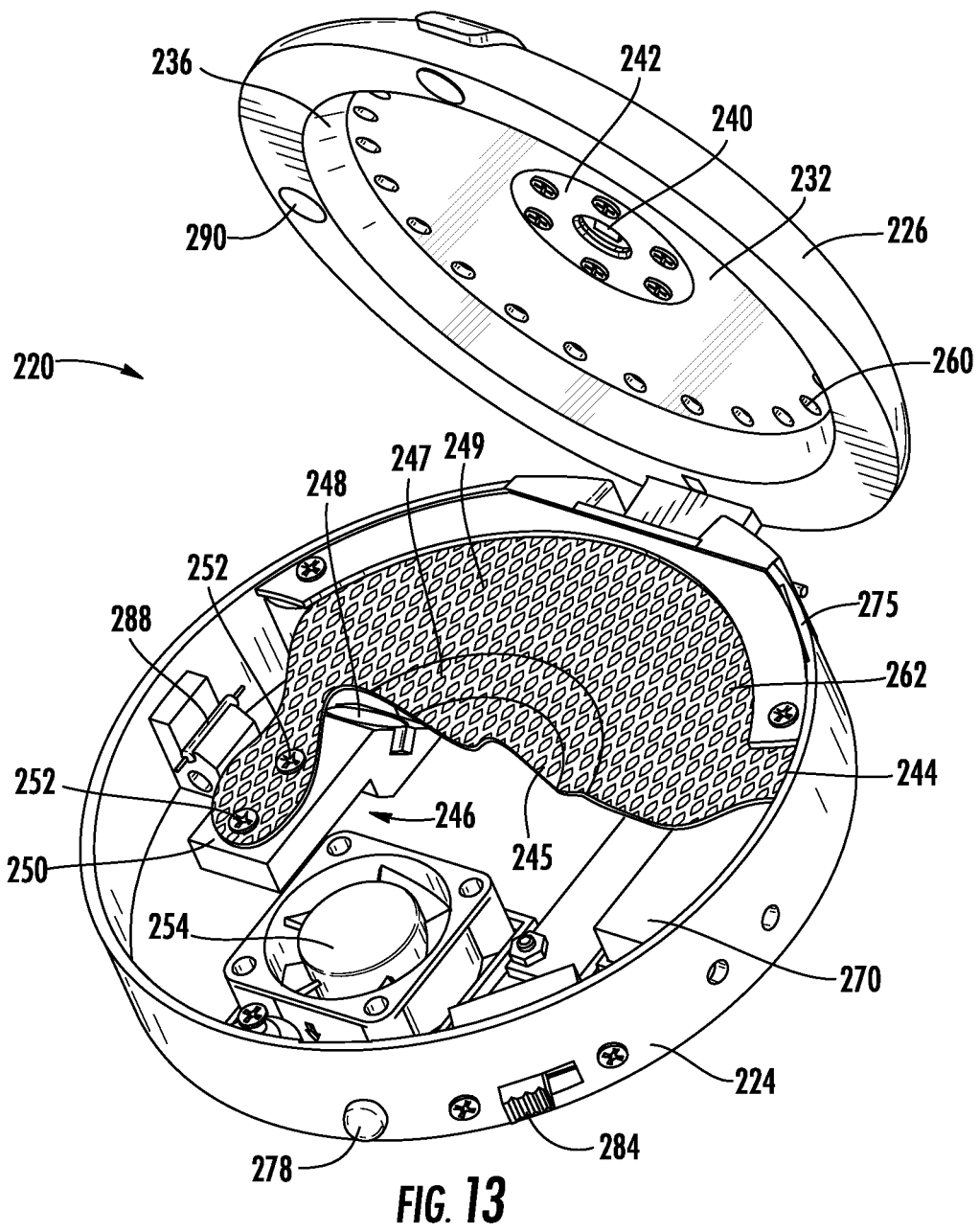
FIG. 13 is a schematic view showing another modified version of the device of FIG. 1.

FIG. 13 shows a modified device 220 in which plate 134 has been eliminated and actuator housing 250 is vibrationally attached directly to support 244 by screws 252. Surface 232 and optionally surface 236 may be UV reflective, although they need not be in all configurations. Support 244 includes portions 245/247/249, although all options and alternatives for the support mentioned above could be employed. In particular, due to the elimination of plate 134, support 244 could be made into a more continuous or fully continuous plate rather than a grid, and/or could be made highly reflective to assist in illuminating target 138. If support 244 is sufficiently reflective, it may be the only reflective surface within device 220. Moreover, support 244 itself need not be reflective, nor are any other surfaces required to be reflective in all aspects of the disclosure. Of course, with lessening or no reflective surfaces, device 220 may have to operate longer, with more or stronger UV emitters, or other compensations may have to be made to clean target 138 as completely as in other configurations.

Figure 14:
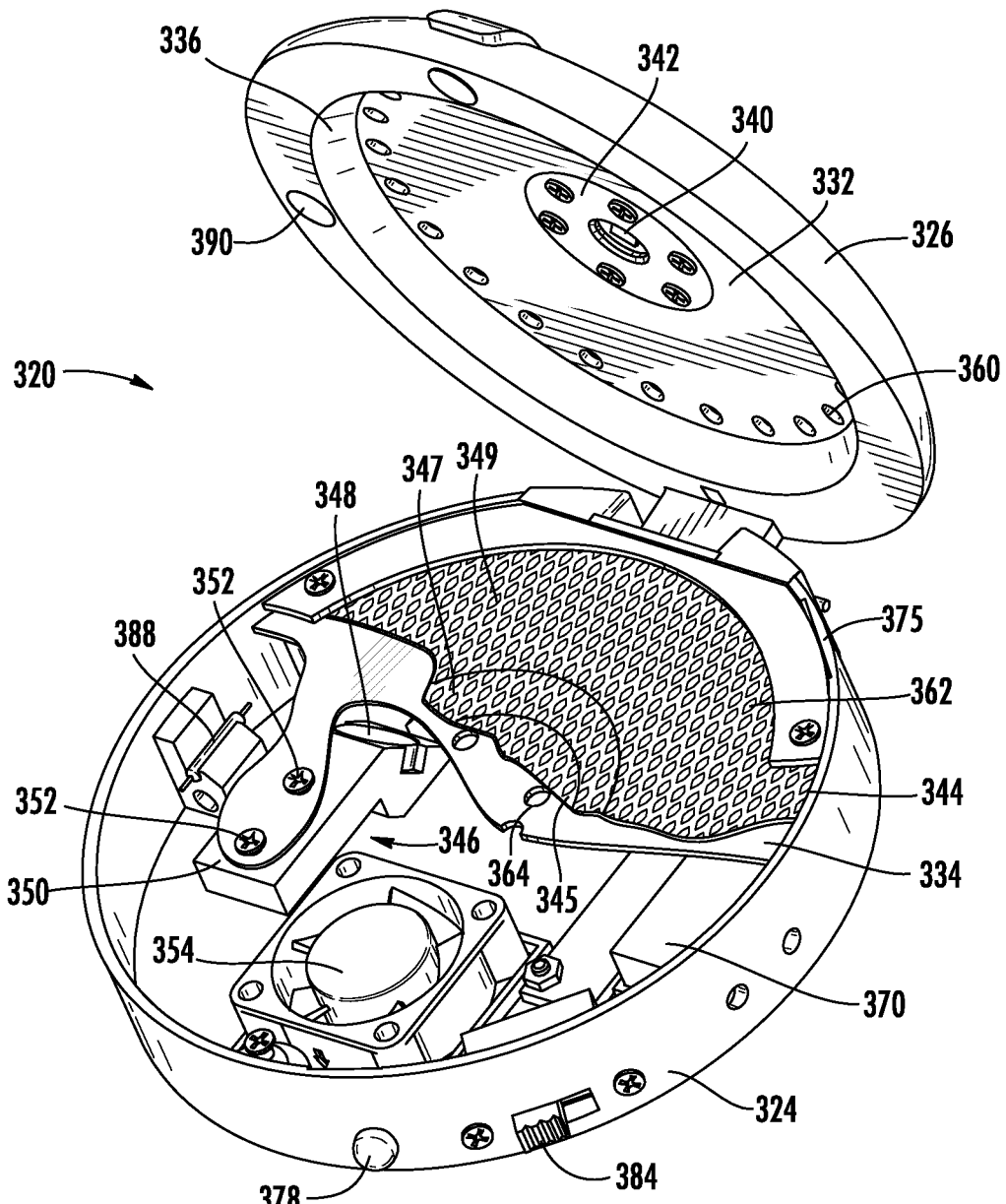
FIG. 14 is a schematic view showing another modified version of the device of FIG. 1.

FIG. 14 shows another alternative device 320 in which lower reflective plate 334 is provided beneath support 344 and is attached to actuator mount 350 by screws 352. Again, support 344 may or may not be reflective. Support 344 is shown with portions 345/347/349, but may be modified as above to have other configurations. Surfaces 332 and 336 are not reflective, but one or both could be.

Figure 20:
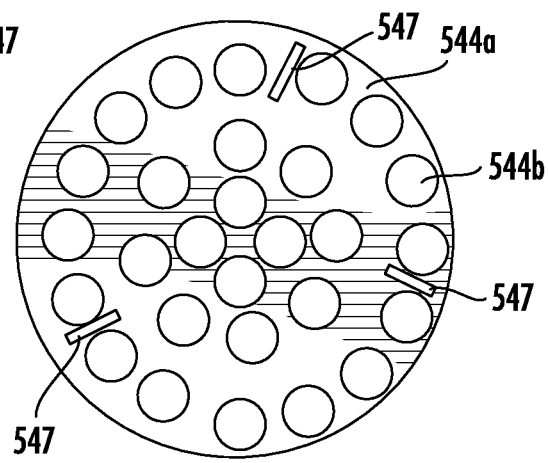
FIG. 20 is a schematic top view a variation on the rotatable holding plate of the assembly of FIG. 19.
Figure 21:
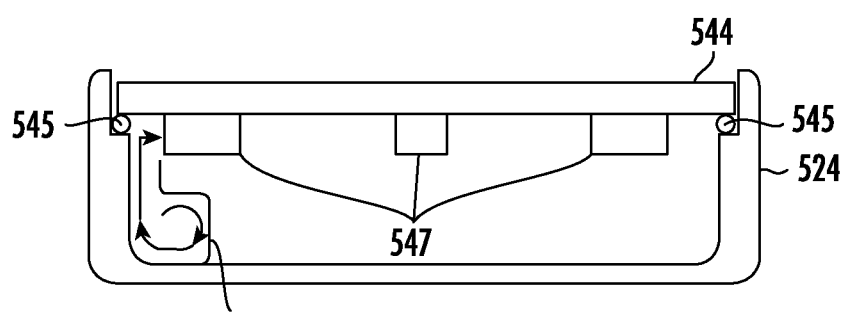
FIG. 21 is a schematic side view of incorporation of the holding plates of FIG. 19 or 20 into a device as disclosed above.

Rotation can be employed to allow different areas of the target to be covered by the light from the light source. If desired, the bottom reflective plate, not the holding plate could instead be rotated relative to the base. Also, if fans are provided for cooling and/or drying, rotation allows such effects to be made more uniform via the rotation. Optionally a cleaning liquid such as water, a disinfectant, alcohol, etc., may be sprayed by a pump within the base into the chamber and/or on to the target for further cleaning. If so, fans in the base may assist with drying the target and/or chamber, and rotation may assist with drying of such cleaning liquids. As shown in FIGS. 20 and 21, the holding plate may be continuous or perforated, as discussed above.

Figure 15:
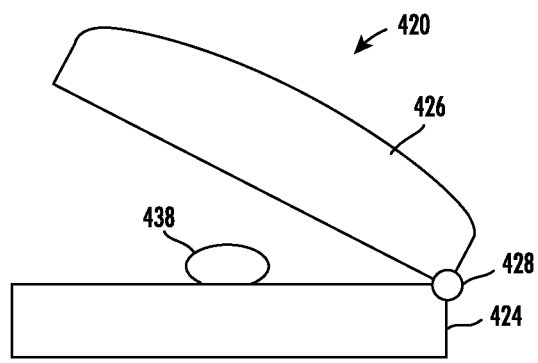
FIG. 15 is a schematic side view showing another modified version of the device of FIG. 1.
Figure 16:
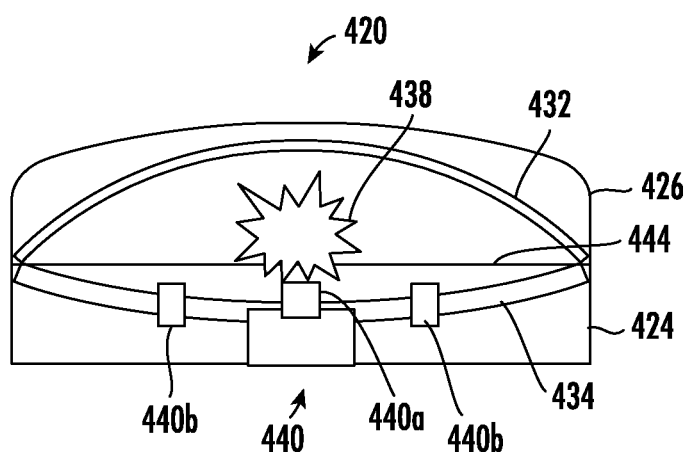
FIG. 16 is a schematic cross-sectional view of the device of FIG. 15.
Figure 17:
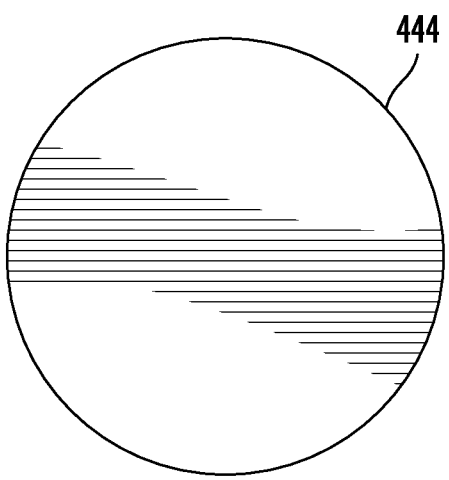
FIG. 17 is a schematic top view of the holding plate of the device of FIG. 15.

FIG. 15-17 schematically show another alternate device 420 with a base 424 and lid 426 connected by a hinge 428. A light source 440 for illuminating the target 438 within a light chamber is mounted in the base 424, beneath a holding plate (support) 444 for holding the target 438. No light source is in the lid. The light source may be one or more of an LED, UV LED, etc., as described above, or the light source may be the outlet of a waveguide for transmitting light from, for example, a UV LED, to a location in which the light can be introduced into the chamber. The light source 440 may be a single localized source 440a, or may include multiple sources 440a and/or 440b. One or more reflective plates 432 and/or 434 may be provided at a top and bottom of the chamber (within lid 426 and base 424, respectively) for reflecting light to improve coverage on the target 488. Placing the light source 440 only in base 424 locates it with other electronics, simplifies electrical connection to the light source, and prevents wear and tear on connecting electronics that might pass through or alongside the hinge between the base and lid.

Figure 18:
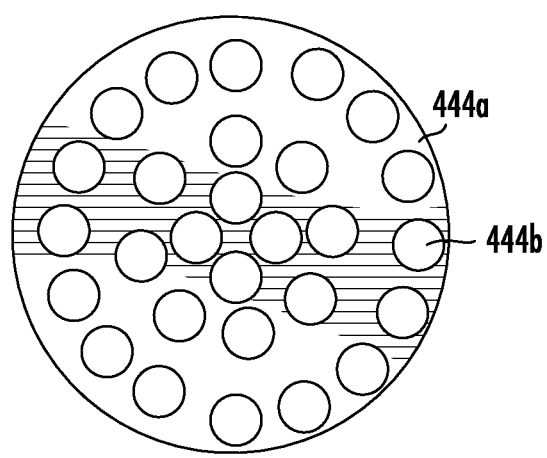
FIG. 18 is a schematic top view of an alternate holding plate for the device of FIG. 15.

As shown, the holding plate/support 444 in FIG. 17 as solid (at least partially translucent/transparent), but it may alternatively be a perforated element 444a with openings 444b, as in FIG. 18 to improve light or airflow transmission, or to allow drainage.

Figure 19:
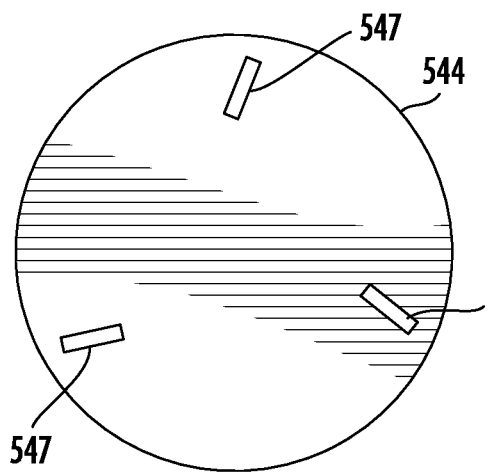
FIG. 19 is a schematic top view of an alternate rotatable holding plate assembly suitable for use with any of the above embodiments.

FIGS. 19-21 show another modified holding plate assembly that could be incorporated into any of the embodiments above. As shown in FIG. 21, holding plate 544 is rotatable on bearings 545 mounted to base 524. Plate 544 includes at least one (three shown) fin 547 that can cooperate with one or more fans 548 in base 524 to effect the rotation of the holding plate to the base. FIG. 20 shows alternative plate 544a with openings 544b for air, light, or liquid transmission. Either type of holding plate may be mounted around its perimeter to the base or structure attached to the base (as shown) and/or mounted centrally (not shown). Thus, the fan and the fins if included, comprise a means for rotating the support relative to the base so that the target moves relative to the at least one UV emitter in the base. Fins are not strictly required, and thus may be replaced by other structures that are inherently part of or that extend from holding plate, whether formed unitarily or added, so that impinging air from one or more fans causes the relative rotation.

Figure 22:
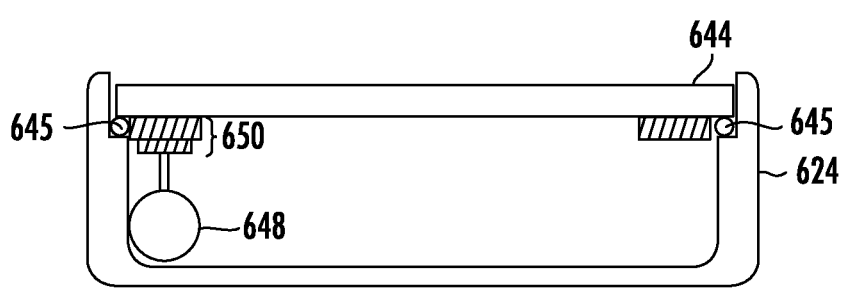
FIG. 22 a schematic side view of an alternate device as disclosed above incorporating an alternate rotatable holding plate.

Alternatively, as shown in FIG. 22, a motor 648 can be provided in the base to effect rotation of the bottom reflector and/or holding plate 644 by mechanical drive connection 650 (geared, frictional, belts and pulleys, etc.), rather than via airflow. Also, actuators such as those provided for vibration noted above can be configured and aligned with a movable holding plate or reflective surface to achieve relative rotation between such structure and the base. Such alternative structures also may comprise a means for rotating the support relative to the base so that the target moves relative to the at least one UV emitter.

Rotation can be employed to allow different areas of the target to be covered by the light from the light source. If desired, the bottom reflective plate, not the holding plate could instead be rotated relative to the base. Also, if fans are provided for cooling and/or drying, rotation allows such effects to be made more uniform via the rotation. Optionally a cleaning liquid such as water, a disinfectant, alcohol, etc., may be sprayed by a pump within the base into the chamber and/or on to the target for further cleaning. If so, fans in the base may assist with drying the target and/or chamber, and rotation may assist with drying of such cleaning liquids. As shown in FIGS. 17-20, the holding plate may be continuous or perforated, as discussed above.

Figure 23:
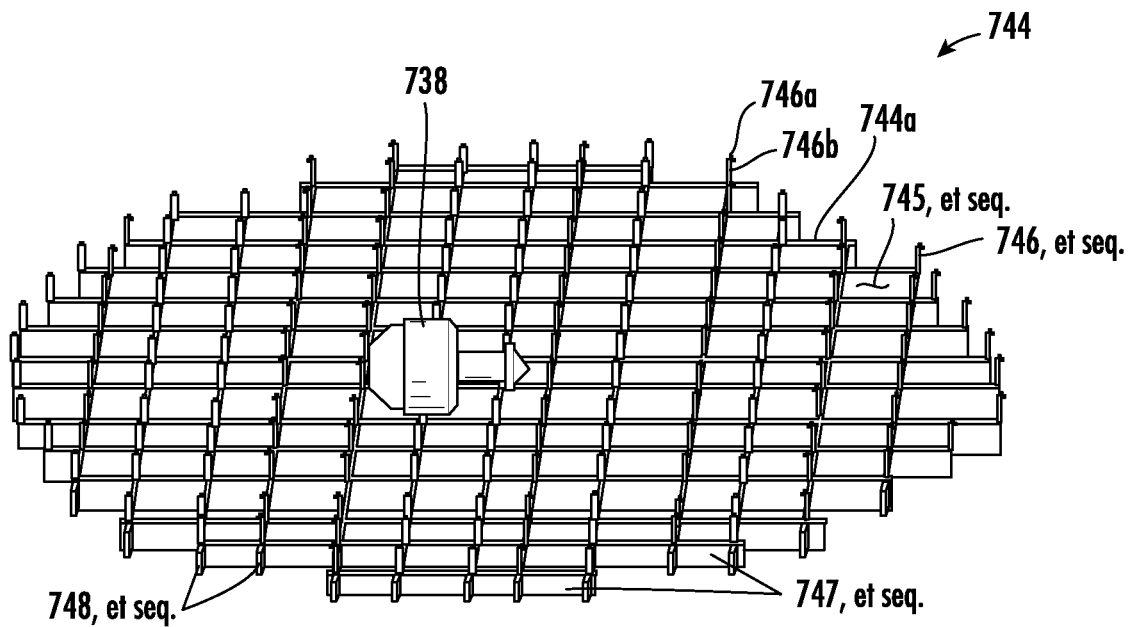
FIG. 23 is an isometric top view of an alternate holding plate suitable for use with any of the embodiments herein.
Figure 24:
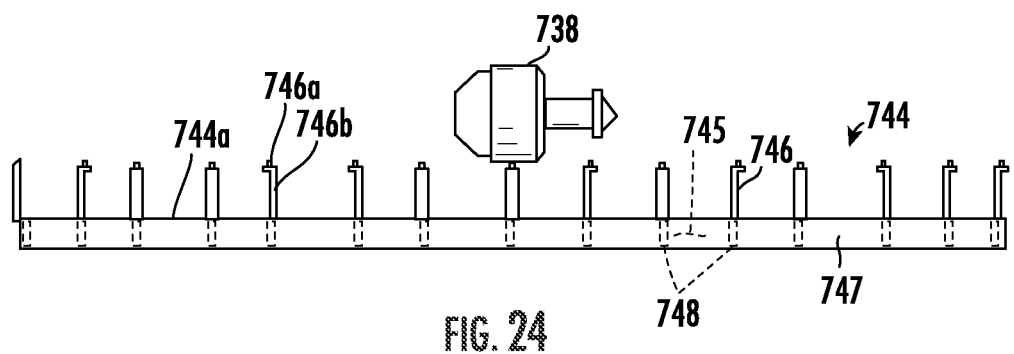
FIG. 24 is a side view of the holding plate of FIG. 23 with a target item thereon.

FIGS. 23 and 24 show another alternate support for holding the target item during irradiation that can be incorporated into any of the embodiments herein. As shown, support 744 is generally round and flat to fit within the housings disclosed herein, but support 744 could have other shapes, in view of housing shape or otherwise. As in other embodiments, support 744 is to be located in the housing chamber between the lid and base. Support 744 is located so as to hold the target item 738 generally between whatever UV reflective surfaces are used so that the UV radiation from whatever UV light sources (e.g., one or more UV LED's or arrays of such) are used illuminate the target item.

Support 744 as illustrated has both openings 745 and protrusions 746 thereon, but either or both may be employed in certain aspects. Openings 745 are formed between intersecting sets of evenly-spaced first ribs 747 and second ribs 748 arranged in an orthogonal grid. Thus, openings 745 are substantially square (when viewed from above). Alternatively, if openings are to be employed, other shapes could be used, such as different (evenly or unevenly spaced) arrangements of ribs, different numbers of sets of ribs (e.g., three sets extending 60 degrees apart instead of two sets extending 90 degrees apart), spiral, curved, or circular ribs, or substitutions of other structures with openings, such as the perforated, mesh-like structures, screens, etc., noted above or others. For structural stability or ease of mounting, a circular outer rib (not shown), mounting structures, flanges, snaps, screw openings, sealing structures, etc., may be added to support 744 as needed to mount support 744 fixedly or movably within the device in various ways.

Openings 745 may also be configured so as to guide illumination and/or airflow toward a desired location on support (i.e., a central location where the target item resides). Thus, some or all of ribs or other sidewalls defining the openings may be non-orthogonal, slanted, etc., to favor transmission of light or airflow from a location or locations to a desired location or locations, in a desired pattern, etc. Openings 745 in grid form (as compared to perforated, mesh-like structures such as in support 44) can provide more light and air transmission per area of the support (viewed from above). Constructing support 74 of ribs extending more in a vertical direction than a horizontal direction also helps increase the amount of the support that is taken up by openings 745. Use of reflective material also helps with light transmission and reflections of the ribs propagate light within the chamber and/or to the target. Openings 745 may thus comprise at least 50% of the surface area of support 744, but may preferably comprise a higher amount, such as 70%, or even 90% as long as structural integrity of support 744 and sufficient support and control of target is maintained.

Thus, use of openings 745 may provide at least one of three or more benefits. First, less material may be used in some designs of a support 744 with openings (as compared to a continuous, plate-like support), lowering weight, and potentially lowering raw material cost. Second, openings 745 can allow direct and/or reflected light transmission therethrough, thereby increasing irradiation to the target item and potentially allowing for alternate locations and/or fewer light sources to provide coverage. Third, airflow for cooling and/or drying can occur, with or without a fan, and with or without other flow path openings throughout the device.

It should be understood that openings 745 are optional. Thus, if an opaque material without openings is employed for support 744, light sources and/or reflective surfaces may be distributed throughout the chamber (including on support 744 itself if desired) to provide sufficient illumination to irradiate the target item. Also, support may be made from transparent or translucent material, with or without openings, to improve transmissibility. Thus, any of the metals, plastics or other materials noted herein for supports may be employed for support 744, and support 744 may be made of different materials (for example, differing material(s) for ribs, an outer ring, protrusions, mounting structures, sealing structures, etc.).

Protrusions 746 may extend upward above upper side 744*a* of support 744 for holding target item 738 above other portions of the support structure (e.g., ribs 747,748 or equivalent if employed, or simply upper side 744*a* if no openings, ribs, etc. are used). As illustrated, protrusions 746 extend upward at each intersection between ribs 747 and 748. However, more or fewer protrusions 746 than shown could be employed. For example, protrusions could extend from only half or one quarter or fewer of such intersections in some embodiments. A sufficient number and arrangement of protrusions may be selected to support target item 738 above support top surface 744*a* in view of the size and shape of the target item and chamber. Protrusions 746 may be differently sized in terms of width, height, or tip shape, may be aligned or angled relative to each other, or may be uniformly or non-uniformly arranged to influence target item 738 to move toward or remain in a desired location (e.g., in the middle of support 744). Thus, protrusions 746 may have a distribution of different overall heights to achieve a distribution (lesser height in middle portion, increasing height in an outward direction, and/or greater height in outer portion), along the lines of FIGS. 11-14, or other distributions. Tips 746*a* of protrusions 746 may have many shapes, such as rounded, pointed, cylindrical, square, enlarged or decreased in size or diameter in a distal direction, etc. Tips 746*a* may include contact portions formed integral with body portions 746*b*, or may include contact portions attached to body portions 746*b*, for example, a protective, non-slip, or lower durometer material for contacting target item 738.

Use of protrusions 746 on support can provide one or more benefits, namely efficient and lightweight design of support 744, improved light transmission and/or airflow to and around target item 738 as compared to a support with openings 745 and no protrusions. Protrusions 746 can be used on supports with or without openings 745. If desired, protrusions 746 can be made of a material more translucent or transparent than other portions of support 744 to improve transmissibility.

Figure 25:
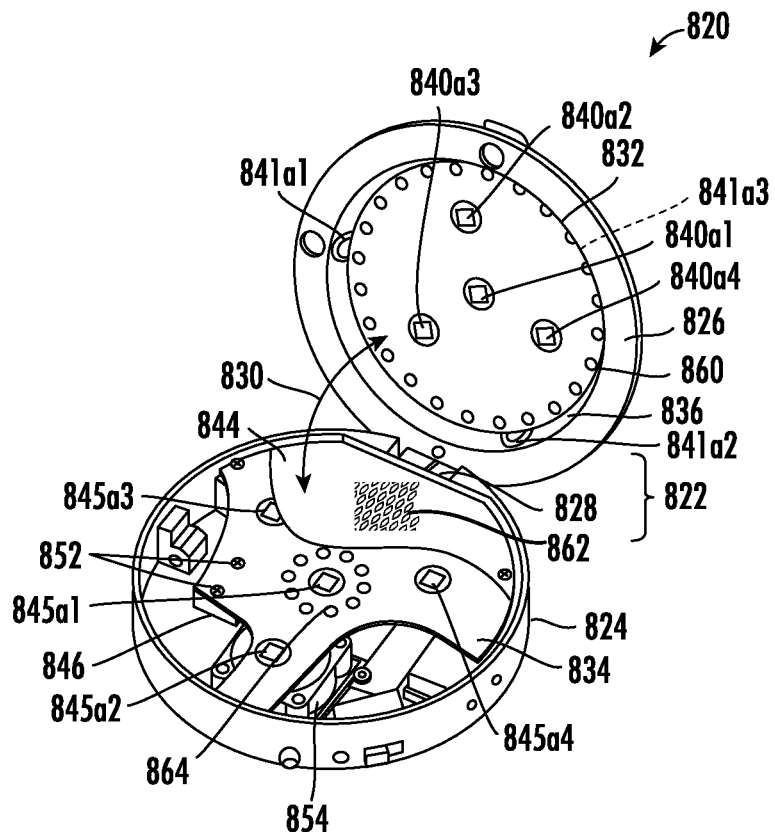
FIG. 25 is an isometric, partially broken-away, top view of another alternate embodiment of a disinfecting device with light sources above and below a support for holding a target item to be irradiated.
Figure 26:
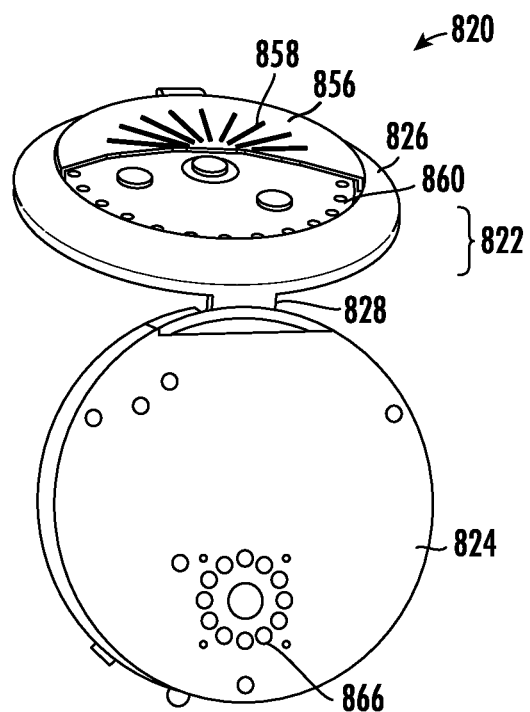
FIG. 26 is an isometric partially broken-away, bottom view of the embodiment of FIG. 25.

FIGS. 25 and 26 show another alternate device 820 for irradiating a target item. Device 820 includes light sources both above and below the support 844 for holding the target item 838. Details of device 820, its light sources, its airflow system, and its actuators are discussed below. Other features may be the same as or similar to corresponding features in one or more of the above embodiments.

As shown in FIG. 25, device 820 includes a housing 822 with a base 824, a lid 826 attached to the base by a hinge 828. Within device 820 is a chamber 830, a first UV reflective plate 832 in lid 826, and a second UV reflective plate 834 in base 824, and an optional third UV reflective surface 836, as shown in lid 826. As above, the reflective surfaces provide a reflective chamber 830 for generally enveloping a target item (not shown, see target item 38 above). As above, plates 832,834 may be curved, for example parabolic or substantially parabolic, and may have identical or differing curvature, although one or both plates may be flat.

At least one light source, such as a UV emitter, and in this case an LED 840a1, may be located along first UV reflective plate 832 within lid 826, and is positioned to emit UV radiation into chamber 830. UV LED 840a1 may be formed in an assembly including typical electric connections and controls, and a heat sink (not shown) for removing heat generated by the UV LED. As shown, LED 840a1 is located centrally within plate 832. Additional LEDs 840a2-840a4 may be located around LED 840a1 within plate 832 (spread 120 degrees apart from each other around LED 840a1 and outward at about half the radius of reflective plate 832). Use of more than one light source in plate 832 may increase distribution and coverage of illumination within chamber 830 and ultimately on the target item. It should be understood that only one, up to four, or more than four light sources, with light sources at one or more differing radii along plate 832 could be used on plate 832 of lid 826 if desired.

If optional reflective surface 836 is employed above support 844 within lid 826 (as shown and/or alternately below support 844 within base 824), at least one additional light source such as a UV emitter, in this case an LED 841a1, may located along surface 836 to emit UV radiation into chamber 830. Device 820 includes three UV LEDS 841a1-841a3 located around surface 836, 120 degrees apart from each other and circumferentially between (interleaved with) UV LEDS 840a2-840a4. Use of one or more LEDs 841a1-841a3 along surface 836 of lid 826 (or of base 824), either in conjunction with or instead of one or more LEDs 840a1-840a4 along plate 832 of lid 826, can further help provide greater distribution and/or power to disinfect the target item. It should be understood that in device 820 many options for arranging light sources in lid 826 are possible. For example, only one light source chosen from UV LEDS 840a1-840a4 and 841a1-841a3 may be used in lid 826; one light source chosen from UV LEDS 840a1-840a4 and one from UV LEDs 841a1-841a3 may be used in lid 826; one or more light sources chosen from UV LEDS 840a1-840a4 and one or more from UV LEDs 841a1-841a3 may be used in lid 826; and more light sources than shown may be employed for either of UV LEDS in plate 832 and UV LEDs in surface 836.

At least one light source such as a UV emitter, in this case an LED 845a1, may be located along second (lower) UV reflective plate 834 below support 844 within base 824, and is positioned to emit UV radiation into chamber 830. UV LED 845a1 may be as above formed in an assembly including typical electric connections and controls, and a heat sink (not shown) for removing heat generated by the UV LED. As shown, LED 845a1 is located centrally within plate 834. Additional LEDs 845a2-845a4 may be located around LED 845a1 within plate 834 (spread 120 degrees apart from each other around LED 845a1 and outward at about half the radius of reflective plate 834. Again, a surface akin to surface 836 may be used below support 844, and may be reflective, and may instead or additionally include one or more light sources therein.

As above, use of more than one light source in plate 834 may increase distribution and coverage of illumination within chamber 830 and ultimately on the target item. If desired, LEDs 845a2-845a4 in lower plate 834 may be circumferentially aligned with LEDs 840a2-840a4 in upper plate 832 and interleaved relative to LEDS 841a2-841a4, although the LEDs within groups could also be spaced, interleaved, arranged differently in a pattern or randomly, etc. It should be understood that only one, up to four, or more than four light sources, with sources located at one or more differing radii along plate 834 could be used on plate 834 of base 824 if desired.

The various light sources noted above may be thus said to be arranged in an array including LEDs from any of the groups above, arranged as shown in FIG. 25 or as suggested with one or more of the various modifications discussed above. There may be particular benefits of an array with a distribution of illumination of having at least one UV LED in lid 826 and at least one UV LED in base 824, although such is not required in all aspects of the disclosure. The distribution in the array may be uniform, partially uniform, non-uniform, or random. Also, each individual light source may comprise a single chip LED, a multichip LED with an array, grid, etc., of multiple emitters, of uniform frequency or of differing frequencies, and uniformly or differently aimed, targeted, lensed, relative to the surface in which they are housed, etc., for a desired spectral and dimensional coverage.

Light sources in lid 826 may be powered from the base 824 by wiring extending from base 824 along or through hinge 828 to lid 826 or via wireless (inductive) power transmission from base 824 to lid 826, or may be powered from the lid 826 by a separate power source (battery) within the lid. Alternatively, sliding contacts could be used, such as metal brush-type contacts or magnetic contacts to transfer power from the base to the light sources and other electronics on the lid. Also, solar collector cells may be used to collect power for storage or immediate provision to light sources.

As above, a support 844 is attached to base 824 and is located in chamber 830 between first UV reflective plate 832 and second UV reflective plate 834. Support 844 locates the target item between first UV reflective plate 832 and second UV reflective plate 834 so that the UV radiation illuminates the target. Support 844 may include any of the options noted above, and may be for example as shown a perforated mesh-like structure extending substantially across chamber 830 within base 824 when lid 826 is closed. Support 844 may also be able to move relative to base 824, as noted above.

As also noted above, at least one actuator 846 may be attached to housing 822, in this case base 824, positioned to move the target item relative to support 844 while light sources emit radiation. Although use of only one such actuator is possible, up to three of such actuators may be provided, mounted in opposing directions so as to create movement in differing planes. Each actuator may be a vibro-actuator attached to base 824, and optionally attached to second UV reflective plate 834 by screws 852. Each vibro-actuator may create linear motion and/or rotational motion, and may be of various types. For example, suitable choices for vibro-actuators include a piezo-actuator, a magneto-striction actuator, an electromagnetic (solenoid) actuator, and electromagnetic (angular) actuator, and/or a vibration motor having a rotating eccentric, whether electric, pneumatic, or hydraulic powered. If desired, vibro-actuators may be mounted so as to create movement along orthogonal axes (for example along the common Cartesian coordinate x, y, and z axes). The actuators may include conventional sensing and control unit to provide a resonance frequency search function to optimize frequency of vibration for improving the amount of movement of the target item during vibration. The actuators are provided to create motion and/or vibration sufficient to move the target relative to UV LED(s) so as to provide differing illumination of the target over time, so as to reduce or eliminate non-uniform irradiation of the target item, and/or to help uniformly dry or provide heat transfer from the target item. If desired, such movement can be of a frequency and amplitude to turn over, rotate, etc., the target item so as to provide coverage of more if not all surfaces of the target. Use of a highly reflective chamber 830 as described above assists with improving UV LED radiation of such coverage so that more uniform coverage is achieved. It should be understood that use of such actuators is not required for all aspects of the disclosure.

If desired, openings may be located throughout device 820 to assist with removal of heat and/or moisture from housing 822. If desired, a fan 854 may be located within base 824, to assist with pulling air through housing 822 and past the target item to assist in drying the target item or removing heat generated by the LEDs or other electronics. One possible flow path through a series of openings is as follows: lid cover 856 may have openings 858, first plate 832 may have openings 860, support 844 may have openings 862, second plate 834 may have openings 864, and base 824 may have openings 866. However, other openings and flow paths are possible thorough housing 822 upstream and downstream of fan 854. The air-flow may go in either direction (lid-to-base or base-to-lid), or may be through lid only or base only, and need not go past or through support 844. As above, fan 854 may be operated continuously, intermittently, before or after the UV LED, based on a sensed temperature, moisture, or humidity level, etc., and may be stopped, started, adjusted, or modulated as desired.

It should be kept in mind that the various options with the various embodiments noted above regarding vibration, number and location of reflective surfaces, plate shape, plate perforation, plate protrusions, and/or transmissivity, etc., can all be applied individually or in groups to the devices of FIGS. 15-26 or vice versa.

Otherwise, the following parameters may be adopted with the FIG. 15-26 embodiments or the earlier embodiments.

One or more of the UV reflectors may have reflectivity of more than 0.1% in the wavelength range of about 200-300 nm. Also, the holding plate may have UV transparency more than 0.1% in the wavelength range about 200-300 nm. If the holding plate is perforated, the UV transparency may be more than 0.1% in the wavelength range of about 200-300 nm, and perforation pattern (opening) size may be less than the size of the object. Although, it should be understood that the holding plate need not be UV transparent. UV transparency and/or reflectivity also does not necessarily have to be more than 0.1% over the entire 200-300 nm range. Transparency and/or reflectivity may be less than that in certain wavelength range(s) except for the disinfection wavelength.

Fans and actuators are optional, and various types of similar and different curvatures of the top and bottom reflectors could be employed for optimized illumination of the target. The curvature of one or more reflectors could be changed by one or more actuators. A surface of one or more of the reflectors and/or the holding plate may be uneven, for example rough surface, polished surface, etc., to provide light diffusion and/or scattering for more uniform illumination of the target. The surface of UV reflector(s) and/or holding plate maybe patterned with pattern size comparable to the disinfection wavelength of light being used.

The UV LED light may be coupled to the chamber through one or more holes in the bottom reflector and/or through a UV transparent window in the bottom reflector. The bottom UV reflector can be (i) a reflecting material, (ii) a UV transparent material with at least one side covered with UV reflecting coating; or (iii) a multi-layered structure with matching UV reflectance/transparency for optimal light waveguiding at disinfection wavelength of light being used. The UV LED light may be coupled to the chamber via waveguiding and multiple reflections inside the bottom reflector with light escape to the chamber through the top surface of the reflector and/or the holding plate.

In view of the above, devices and methods are disclosed in FIGS. 15-26 modifying or adding to the disclosed subject matter of FIGS. 1-10. Aspects from each of the embodiments may be used apart from the remaining aspects of their respective embodiments and may be combined in various ways with other aspects of this disclosure. Thus, the disclosed devices and methods may incorporate changing the shape of or eliminating any one, two, or all of the UV reflective plates by modifying the surface profile and/or reflectivity of the support, by providing vertical vibration (in combination or alone) sufficient to cause the target to flip over on the support, by the configuring actuator mount in different ways or by connecting the actuator mount to different elements, by providing an air flow from fan (or an additional fan) to help keep the target centered beneath the UV emitter, etc.

While preferred embodiments of the invention have been described above, it is to be understood that any and all equivalent realizations of the present invention are included within the scope and spirit thereof. Thus, the embodiments depicted are presented by way of example only and are not intended as limitations upon the present invention. Thus, while particular embodiments of the invention have been described and shown, it will be understood by those of ordinary skill in this art that the present invention is not limited thereto since many modifications can be made. Therefore, it is contemplated that any and all such embodiments are included in the present invention as may fall within the literal or equivalent scope of the appended claims.

The invention claimed is:

1. A device for cleaning a target comprising:
   a housing including a base defining an inner circumference and a lid, the housing defining a vertical axis extending through a center of the base and lid;
   a chamber within the housing having a top within the lid, a bottom within the base, and at least one UV reflective plate in the lid and at least one UV reflective plate in the base, both of the at least one UV reflective plates being non-planar;
   at least two UV emitters attached to the at least one UV reflective plate in the lid and positioned to emit UV radiation into the chamber, the at least two UV emitters in the lid being located and oriented so that a line defined by a center of emitted UV radiation of each is oriented at a different angle with reference to the vertical axis;
   at least two UV emitters attached to the at least one UV reflective plate in the base and positioned to emit UV radiation into the chamber, the at least two UV emitters in the base being located and oriented so that a line defined by a center of emitted UV radiation of each is oriented at a different angle with reference to the vertical axis; and a support attached to the base and located in the chamber, the support configured for locating the target between the UV reflective plates so that the UV radiation from the UV emitters illuminates the target, the support formed of a plurality of ribs configured to fill the inner circumference so that the target is supported thereon without falling onto the base, spaces being defined between the ribs sufficient to allow air flow and light propagation through the spaces.

2. The device of claim 1, wherein the ribs are arranged in an intersecting grid.

3. The device of claim 2, wherein the support further includes a plurality of protrusions extending from a top surface of the support toward the lid.

4. The device of claim 3, wherein a sufficient number of the ribs are provided so that the target rests on upper tips of the protrusions rather than on the ribs.

5. The device of claim 3, wherein the ribs are arranged in an intersecting grid defining a plurality of intersections, and at least some of the protrusions are located at respective ones of the intersections.

6. The device of claim 1, wherein at least one of the at least at least two UV emitters in the lid and the at least two UV emitters in the base each includes an array of UV emitters, wherein each array of UV emitters includes an emitter located along the vertical axis and at least two emitters spaced radially away from the vertical axis.

7. A device for cleaning a target comprising:
a housing including a base defining an inner circumference and a lid, the housing defining a vertical axis extending through a center of the base and lid;
a chamber within the housing having a top within the lid, a bottom within the base, and at least one UV reflective plate in the lid and at least one UV reflective plate in the base, both of the at least one UV reflective plates being non-planar;
at least two UV emitters attached to the at least one UV reflective plate in the lid and positioned to emit UV radiation into the chamber, the at least two UV emitters in the lid being located and oriented so that a line defined by a center of emitted UV radiation of each is oriented at a different angle with reference to the vertical axis;
at least two UV emitters attached to the at least one UV reflective plate in the base and positioned to emit UV radiation into the chamber, the at least two UV emitters in the base being located and oriented so that a line defined by a center of emitted UV radiation of each is oriented at a different angle with reference to the vertical axis; and
a support attached to the base and located in the chamber, the support configured for locating the target between the UV reflective plates so that the UV radiation from the UV emitters illuminates the target, the support including a plurality of protrusions extending from a top surface of the support toward the lid for supporting the target therein thereon without falling onto the base.

8. The device of claim 7, wherein the support is formed of a plurality of ribs configured to fill the inner circumference so that the target is supported thereon without falling onto the base, spaces being defined between the ribs sufficient to allow air flow and light propagation through the spaces, the ribs being arranged in an intersecting grid defining a plurality of intersections, and at least some of the protrusions are located at respective ones of the intersections.

9. The device of claim 7, wherein the at least two UV emitters in the lid and the at least two UV emitters in the base each includes an array of UV emitters, wherein each array of UV emitters includes an emitter located along the vertical axis and at least two emitters spaced radially away from the vertical axis.

10. A device for cleaning a target comprising:
a housing including a base and a lid;
a chamber within the housing having a top within the lid, a bottom within the base, the housing defining a vertical axis extending through a center of the base and lid and through a center of the chamber;
at least one UV reflective plate in the base of the housing;
at least one UV reflective plate in the lid of the housing;
both of the at least one UV reflective plates being non-planar;
at least two UV emitters attached to the at least one UV reflective plate located in the base of the housing and positioned to emit UV radiation into the chamber, the at least two UV emitters in the base being located and oriented so that a line defined by a center of emitted UV radiation of each is oriented at a different angle with reference to the vertical axis;
at least two UV emitters attached to the at least one UV reflective plate located in the lid of the housing and positioned to emit UV radiation into the chamber, the at least two UV emitters in the lid being located and oriented so that a line defined by a center of emitted UV radiation of each is oriented at a different angle with reference to the vertical axis; and
a support attached to the housing and located in the chamber, the support configured for locating the target between the UV reflective plates so that the UV radiation from the UV emitters illuminates the target.

11. The device of claim 10, wherein the at least one UV reflective plate in the lid includes a main plate and a side plate extending circumferentially around the main plate, the at least two UV emitters in the lid including at least one UV emitter in the main plate and at least one UV emitter in the side plate.

12. The device of claim 11, wherein the UV emitters in the main plate and the UV emitters in the side plate are circumferentially interleaved with each other.

13. The device of claim 10, wherein the support is at least one of translucent, transparent, reflective, or formed with openings for transmitting UV light therethrough.

14. The device of claim 10, wherein the UV emitters each include a UV LED or a waveguide outlet for a UV LED.

15. The device of claim 1, wherein the at least one UV reflective plate in the lid includes a main plate and a side plate extending circumferentially around the main plate, the at least two UV emitters in the lid including at least one UV emitter in the main plate and at least one UV emitter in the side plate.

16. The device of claim 15, wherein the UV emitters in the main plate and the UV emitters in the side plate are circumferentially interleaved with each other.

17. The device of claim 1, wherein the support is at least one of translucent, transparent, reflective, or formed with openings for transmitting UV light therethrough.

18. The device of claim 1, wherein the UV emitters each include a UV LED or a waveguide outlet for a UV LED.

19. The device of claim 7, wherein the at least one UV reflective plate in the lid includes a main plate and a side plate extending circumferentially around the main plate, the at least two UV emitters in the lid including at least one UV emitter in the main plate and at least one UV emitter in the side plate.

20. The device of claim 19, wherein the UV emitters in the main plate and the UV emitters in the side plate are circumferentially interleaved with each other.

21. The device of claim 7, wherein the support is at least one of translucent, transparent, reflective, or formed with openings for transmitting UV light therethrough.

22. The device of claim 7, wherein the UV emitters each include a UV LED or a waveguide outlet for a UV LED.

* * * * *